United States Patent [19]

Allen et al.

[11] Patent Number: 5,411,481
[45] Date of Patent: May 2, 1995

[54] SURGICAL PURSE STRING SUTURING INSTRUMENT AND METHOD

[75] Inventors: William J. Allen, Stratford; George Jessup, Brookfield; Frederick F. Ahari, Southport, all of Conn.; Robert A. Rabiner, Middletown, N.J.; John E. Burbank, III, Ridgefield, Conn.

[73] Assignee: American Cyanamid Co., Wayne, N.J.

[21] Appl. No.: 967,033

[22] Filed: Oct. 27, 1992

Related U.S. Application Data

[63] Continuation-in-part of Ser. No. 865,234, Apr. 8, 1992, abandoned, and Ser. No. 927,969, Aug. 11, 1992, abandoned.

[51] Int. Cl.$^6$ ............................................. A61B 17/00
[52] U.S. Cl. ............................... 606/144; 606/139; 606/151; 606/205; 606/207; 606/208
[58] Field of Search .............. 606/139, 142, 143, 144, 606/145, 148, 151, 205-208

[56] References Cited

U.S. PATENT DOCUMENTS

| | | | |
|---|---|---|---|
| 3,687,138 | 8/1972 | Jarvik | 606/205 |
| 4,915,107 | 4/1990 | Rebuffat et al. | 606/144 |
| 4,950,273 | 8/1990 | Briggs | 606/205 |
| 5,035,701 | 7/1991 | Kabbara | 606/148 |
| 5,100,421 | 3/1992 | Christoudias | 606/147 |
| 5,147,373 | 9/1992 | Ferzli | 606/148 |
| 5,149,329 | 9/1992 | Richardson | 604/272 |
| 5,156,633 | 10/1992 | Smith | 606/205 |
| 5,188,636 | 2/1993 | Fedotov | 606/139 |
| 5,234,443 | 8/1993 | Phan et al. | 606/205 |
| 5,254,130 | 10/1993 | Poncet et al. | 606/206 |
| 5,257,637 | 11/1993 | El Gazayerli | 606/148 |
| 5,275,608 | 1/1994 | Forman et al. | 606/170 |

FOREIGN PATENT DOCUMENTS

0708659  7/1931  France ............................ 606/144

Primary Examiner—Stephen C. Pellegrino
Assistant Examiner—Jeffrey A. Schmidt
Attorney, Agent, or Firm—Charles F. Costello, Jr.

[57] ABSTRACT

A purse string suturing instrument is provided for quickly and effectively forming a purse string suture in tubular tissue through relatively small cannulas placed in the body. The instrument includes a pair of elongated jaws, each having a row of spaced-apart uniform-size teeth. The jaws are hinged together at one end to clamp the tubular tissue therebetween. The two rows of teeth are offset with respect to each other so that they mesh when the jaws are closed. The jaws are inserted through a cannula and positioned to close around the tissue to be sutured. The rows of teeth then bend the tissue between them into a wavelike configuration. A pair of needles, the ends of each being connected to a single length of suture, is then inserted through passageways provided through the teeth. An encircling series of stitches are thus formed in the wall of the tubular tissue to create a purse string suture. The needles and the suturing instrument are then withdrawn through the cannula. The tubular tissue can be snugly fitted over an anastomosis ring or the like by drawing and tying the purse string suture.

16 Claims, 27 Drawing Sheets

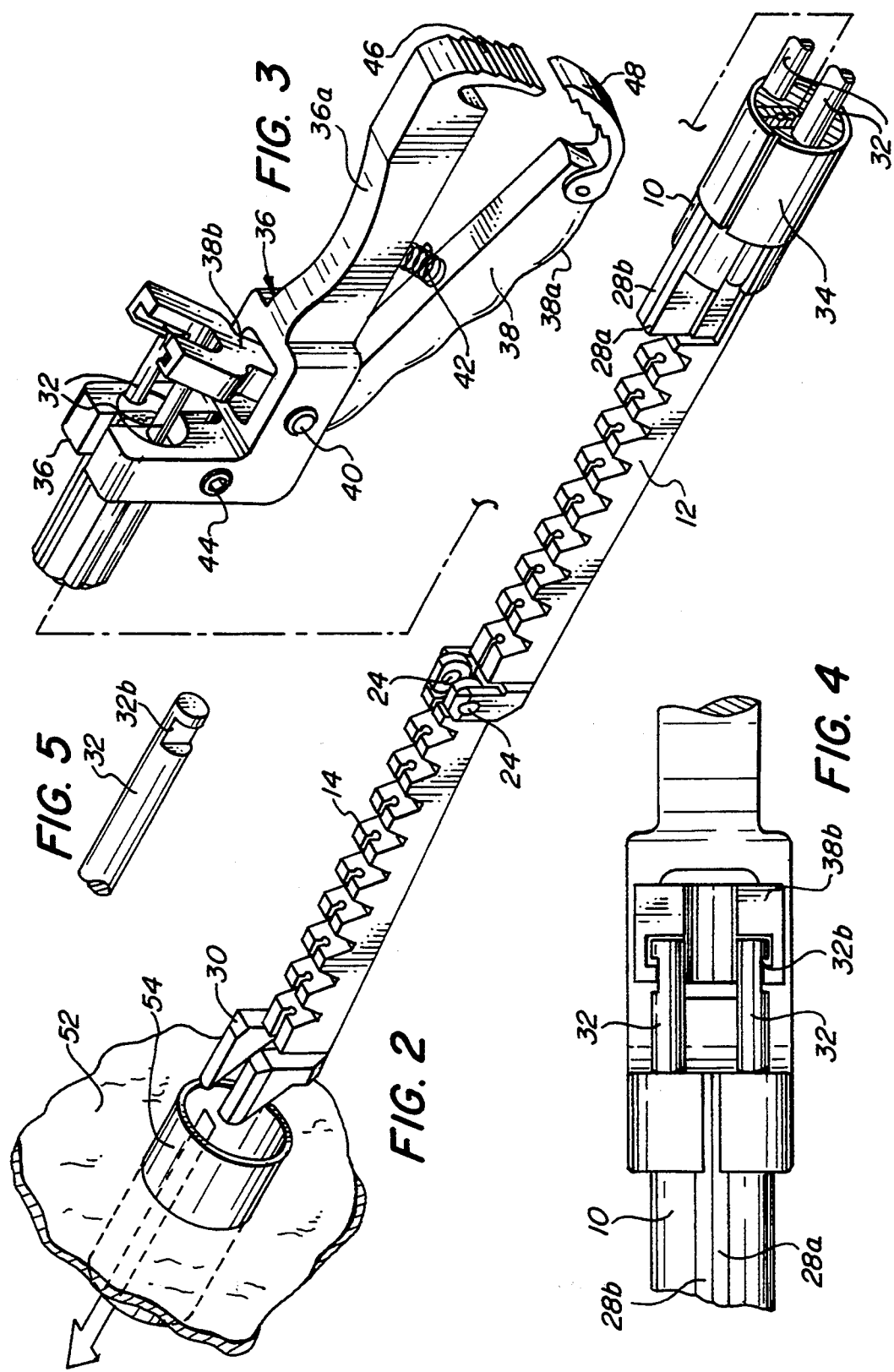

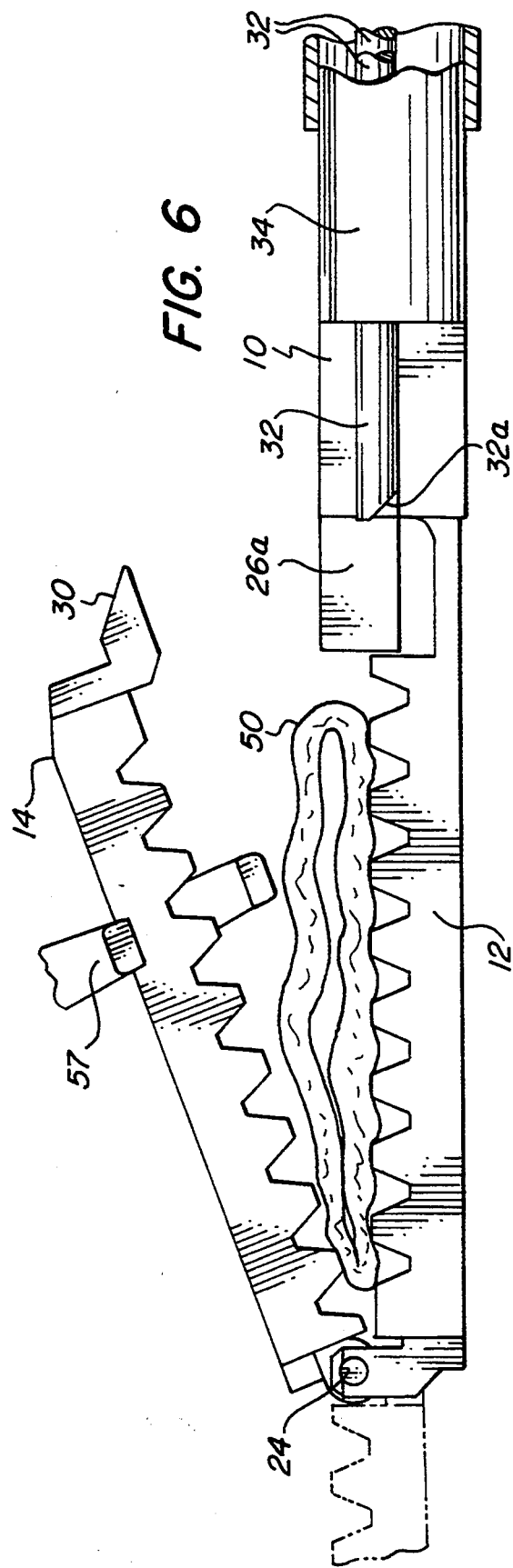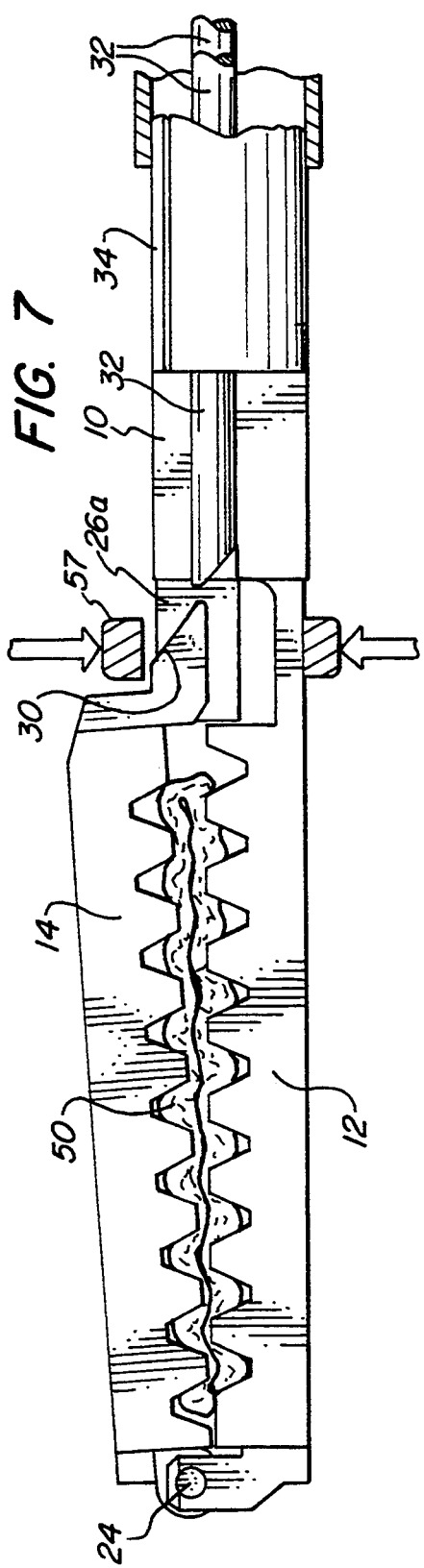

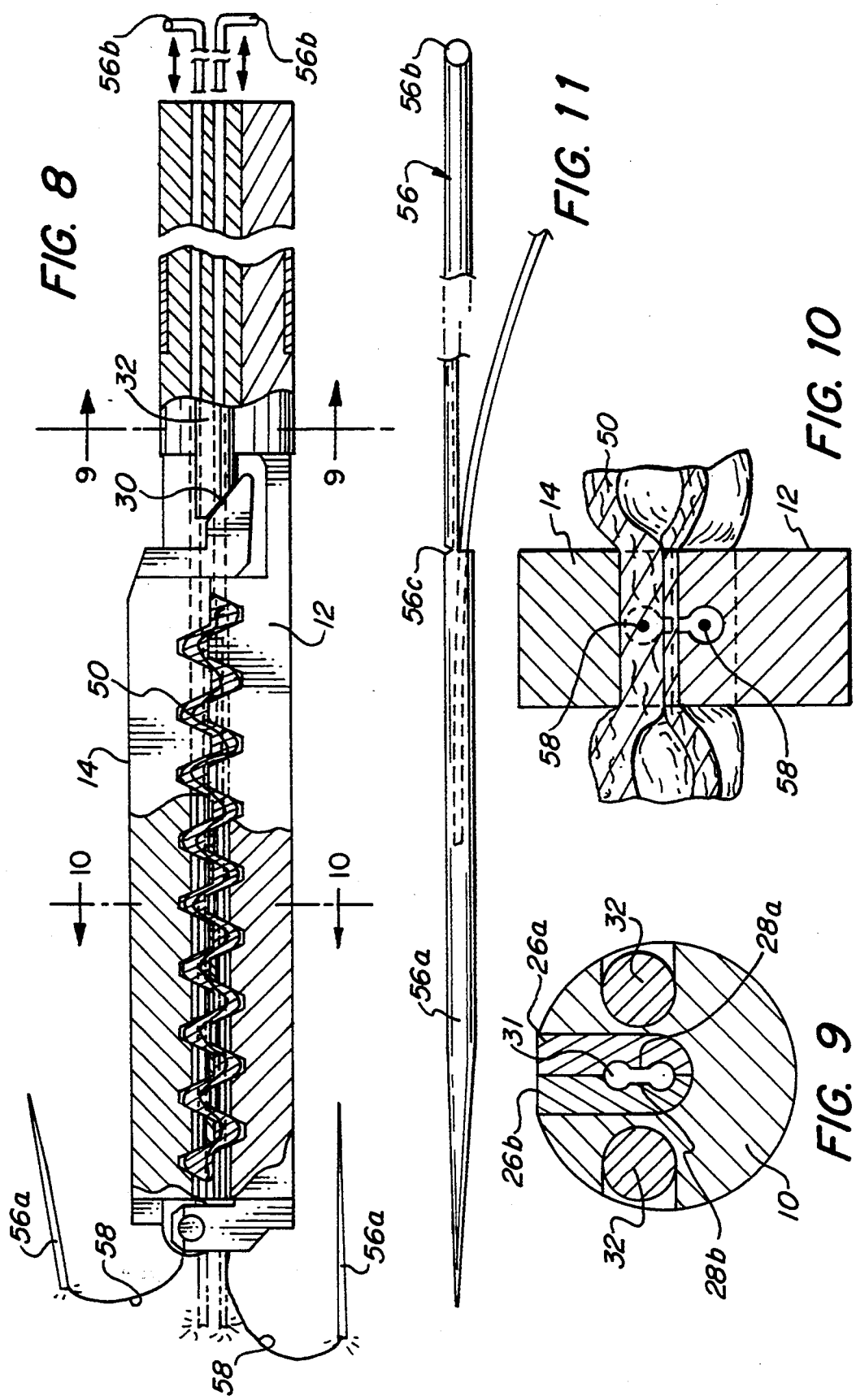

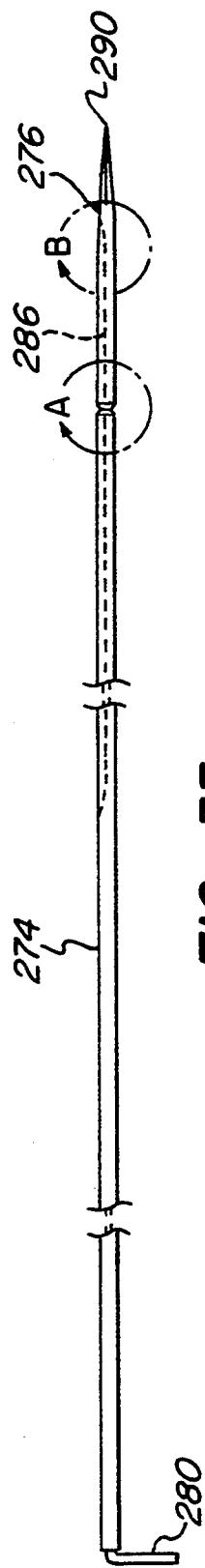
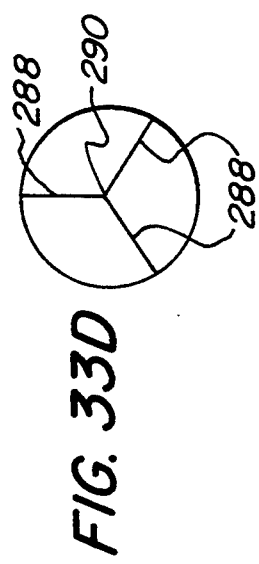
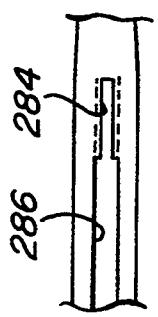
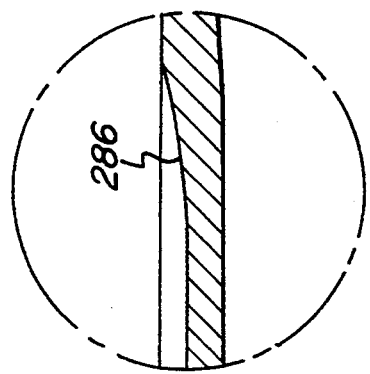
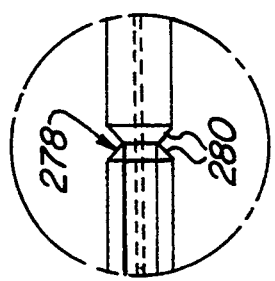

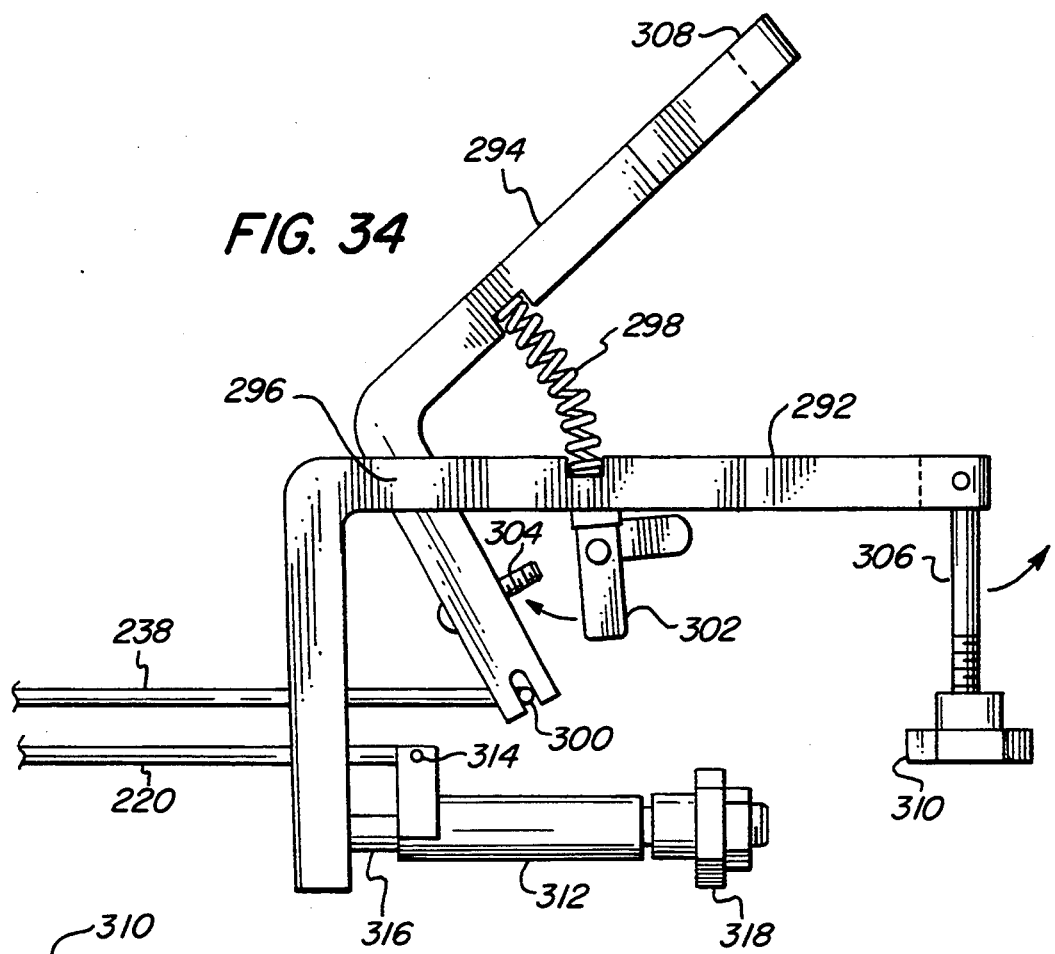
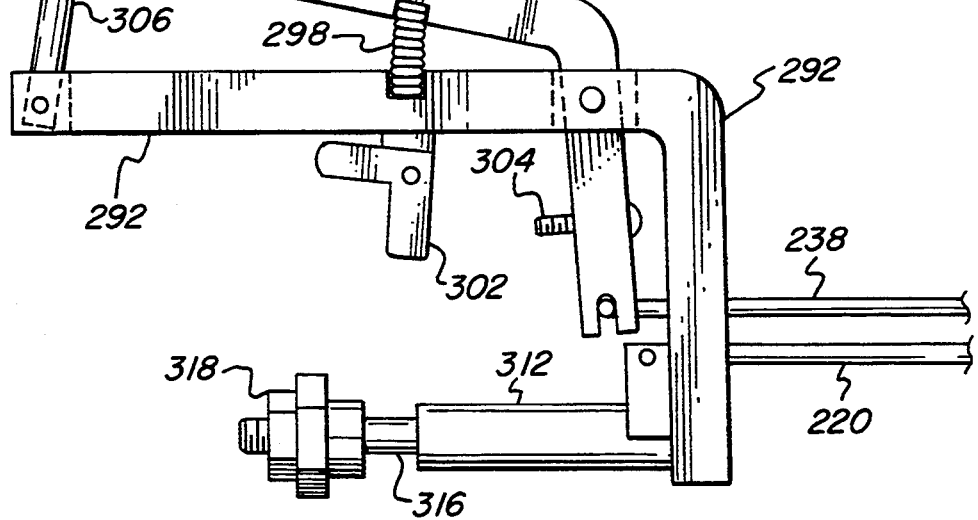

SURGICAL PURSE STRING SUTURING INSTRUMENT AND METHOD

BACKGROUND OF THE INVENTION

This application is a continuation in part of U.S. patent applications Ser. No. 07/865,234, filed Apr. 8, 1992, now abandoned, and Ser. No. 07/927,969 filed Aug. 11, 1992, now abandoned.

FIELD OF THE INVENTION

The present invention relates to a method of placing a purse string suture in a bowel or other section of tubular tissue and to instruments for performing the procedure quickly and without having to open the patient completely.

It is sometimes necessary in performing operations on sections of the alimentary canal to have to put a purse string suture in that tubular tissue. This occurs, for example, when the severed ends of a bowel are rejoined by anastomosis. A biofragmentable anastomosis ring is used to provide a mechanically locking connection that maintains contact between the ends of the intestine in an inverted anastomosis. A purse string suture is used to draw each of the severed ends of the intestine snugly around the barrel of the ring. The ring produces secure serosa-to-serosa apposition of the ends of the intestine and maintains a satisfactory patency until healing occurs and the ring degrades into small harmless fragments, which are eliminated from the body. Anastomosis rings are used in the treatment of various disease processes for which intestinal resection and anastomosis is indicated, for example, carcinoma, diverticular disease, and colostomy closure. A description of the procedure may be found, for example, in U.S. Pat. Nos. 4,467,804; 4,552,148 and 4,766,898.

Placing a purse string suture in tubular tissue has generally required fully opening the body cavity. It would be desirable if there were a procedure for doing so without such a large incision, for example by accessing the body cavity through one or two cannulas instead.

SUMMARY OF THE INVENTION

It is a principal object of the present invention to provide a method and instrument for quickly and effectively putting a purse string suture in a bowel or other section of tubular tissue.

It is a further object of the invention to provide a method and means for putting a purse string suture in a tubular tissue using techniques known as least or minimally invasive surgery without having to fully open the body cavity.

These and other objects are achieved by use of the surgical purse string suturing instrument of the present invention.

In accordance with a first aspect of the invention, the framework of the suturing instrument is a pair of elongated jaws hinged together at one end for swinging in a planar arc of at least about 180 degrees and clamping across the tubular tissue. Each of the jaws has a row of spaced-apart, uniform-size teeth. The two rows are opposed and offset with respect to each other so that the rows of teeth mesh when the jaws are closed. In doing so, the two rows of teeth bend the tissue between them into a wavelike configuration. Because the tube of tissue is collapsed, a two-wall thickness of the tissue overlies the crest of each tooth. Cut into the crest of each tooth is a channel that runs parallel to the direction of the row of teeth. All of these channels in each row are aligned so as to define a substantially straight passageway at their bottoms, which is segmented or interrupted by the gaps between the teeth. This passageway permits the transit of a thread-pulling needle through all of the teeth in the row. The bottom of the segmented channel is sufficiently close to the bases of the teeth that when a needle is forced through the passageway, with the jaws clamped across the tissue, the needle can pierce and run through the wall of the wave of tissue overlying and contacting the crest of each tooth but avoid penetrating the next adjacent wall of tissue. In this way, the needle threads the suturing material through only the wall of tissue that contacts the teeth through which the needle passes, and does not sew the tube closed. By forcing two needles attached to opposite ends of a length of suturing thread completely through the passageways and the tissue (one needle for each passageway), one creates an encircling series of stitches in the wall of the tubular tissue. Each needle can be severed near the suture and removed and the jaws of the instrument can then be opened and the tissue released. The good end of the tissue can then be placed over an anastomosis ring or the like. Then the thread can be drawn snugly and its ends tied together in the conventional manner of knotting a purse string suture.

Because the needle passageway is the bottom of a channel cut into the crest of each tooth, when the jaws are opened the suturing thread slides through the channels and free of the teeth. Preferably, the cross-section of the channel through each tooth is substantially keyhole shaped. The round section is at the bottom of the channel and the narrower width slot section extends from the round section to the crest of the tooth. Using this preferred embodiment, needles having a diameter small enough to fit through the round section but too large to enter the slot can be used. This serves to hold the needle in the desired position at the bottom of the channel, while allowing the smaller-diameter thread to be released when the jaws are opened.

By providing for the jaws of the instrument to swing open at least about 180 degrees, the instrument can be inserted into the body in the fully open position through a first cannula. The trailing jaw is then positioned against the section of tubular tissue to be sutured, transverse thereto. By accessing the instrument through a second cannula, the leading jaw can then be swung closed, thereby clamping the tissue between the two rows of teeth. A novel clamping arrangement is operable from outside the patient's body to secure the jaws tightly together. The surgeon, working outside the wound, can then force the thread-carrying needles into the two passageways in the instrument by pushing with his thumbs on the rear ends of the needles. For that purpose the rear ends should be blunted, for example bent 90 degrees. Once the front ends of the needles protrude a sufficient distance beyond the hinged ends of the jaws to expose the thread, the ends of the thread can be grasped by forceps through the second cannula and cut to release them from the needles. While holding the thread ends to prevent the ends from being pulled back out of the tissue, the needles can then be withdrawn from the instrument. After that the leading jaw can be swung fully open and the instrument withdrawn through the first cannula.

In an alternative procedure, each end of the thread is attached to its needle at a point intermediate the ends of the needle, and each needle has a notch in it, near the point of attachment, but between that point and the rear end of the needle. The notch in the needle is sufficiently deep that if and when the needle is subjected to a bending force sufficient to break the needle, it will break at the notch. Using this embodiment, when the front ends of the needles protrude far enough from the hinged ends of the jaws to expose the thread, the point ends can be grasped with forceps through the second cannula and bent and broken. Then the needle shanks can be withdrawn from the instrument, following which the thread can be cut and the needle points withdrawn through the second cannula. With this arrangement it is less likely that the ends of the thread will be inadvertently withdrawn back through the instrument when the needles are withdrawn. This is because the needle points present a rigid body to be grasped by the forceps and because the needle points present a larger profile that could catch on the channels of the teeth.

Preferably the teeth in this novel suturing instrument are wider at their base than at their crest, when measured in the direction of two rows.

Preferably the instrument will include stop means for limiting the arc of swing of the jaws to a value within the range of about 181 to 187 degrees. This helps guard against the leading jaw jackknifing closed as the instrument is inserted into the body through the first cannula.

It is also preferred that the instrument of the present invention further include camming means for tightening the jaws against each other when they are closed, as well as remote operating means for driving the camming means from a location outside a patient's body when the jaws are to be clamped across a section of tubular tissue inside the body. Further preferred is that the instrument include means for releasably locking the jaws together after they have been tightened against each other by operation of the camming means. It is also preferred that the locking means be operable from outside the patient's body.

A preferred camming means is one that includes a pair of inclined planes or ramps that are integral with an upper, first one of the jaws and are located on or near the unhinged end of the jaw. Such an inclined plane should lie on each side of the needle passageway. Each of the planes should be sloped in a lengthwise direction with respect to the jaw. The direction of the slope of the plane should be such that end of the plane that lies nearer the lower, second jaw when the jaws are closed is also the end of the plane that lies nearer the unhinged end of the upper, first jaw. The purpose for this will be clear in a moment.

This preferred camming means will also include an elongated housing or main shaft having a proximal end and a distal end. The housing is attached at its distal end to the unhinged end of the second jaw so as to extend lengthwise therefrom. The housing includes two slots extending the length thereof. The slots are so positioned as to be aligned with the inclined planes when the jaws are closed. A drive rod is mounted in each of the slots that one of its ends abuts the inclined plane with which it is paired. To push the drive rods, the operating means includes a lever assembly mounted on the proximal end of the elongated housing. This lever mechanism permits the rods to be alternately pushed against the inclined planes and pulled away from them. Because of the orientation of the inclined planes, when the rods are pushed against them, they tend to cam the jaws more tightly closed. The lever assembly is preferably hand-operable and includes biasing means (e.g., a compression spring or the like) tending to urge the rods away from the inclined planes.

It is also preferred that the elongated housing include a pair of lengthwise, internal conduits that align with the needle passageways when the jaws are closed. These conduits should be approximately the same diameter as the needle passageways. Also, in order to permit the thread to pass through the housing, the two conduits must be connected together throughout their length by a slot, preferably a slot having approximately the same width as the slot sections of the channels through the teeth.

In another aspect of the present invention, the framework of the instrument is a main shaft; a pair of relatively movable jaws for clamping the tubular tissue therebetween, the first jaw being substantially pivotable through 180 degrees with respect to the second jaw about a first pivot axis on the main shaft, each jaw having a row of spaced-apart, uniform-size teeth; and a mechanism for moving the first jaw substantially 180 degrees from an insertion position along the main shaft to a second position where the row of teeth of the first jaw meshes with the row of teeth of the second jaw. By using such an instrument, the two rows of teeth bend the tissue between them into a wave-like configuration. Because the tube of tissue is collapsed, a two-wall thickness of the tissue overlies the crest of each tooth. Each tooth is of the same configuration as discussed above so the needle threads the suturing material through only the wall of tissue that contacts the teeth through which the needle passes, and does not sew the tube closed. By forcing two needles attached to opposite ends of a length of suturing thread completely through passageways formed by the channels in each row of teeth and the tissue (one needle for each passageway), an encircling series of stitches is created in the wall of the tubular tissue. Each needle can be severed near the suture and removed and the jaws of the instrument can then be opened and the tissue released. The good end of the tissue can then be placed over an anastomosis ring or the like. Then the suture can be drawn snugly and its ends tied together in the conventional manner of knotting a purse string suture.

By providing for the jaws of the instrument to relatively swing open about 180 degrees, the instrument can be inserted into the body in the fully open position through a cannula, without fully opening the patient. The first jaw is swung from the insertion position about the first pivot axis to an intermediate position adjacent the second jaw. The first and second jaws are then pivoted about second and third pivot axes, which are orthogonal to the first pivot axis. Afterwards, the first and second jaws are positioned adjacent and transverse to the section of tubular tissue and sufficient clamping pressure is applied to the jaws to bend the clamped tissue into a wave-like configuration with a two-wall thickness of the tissue overlying the crest of each tooth, the tissue being forced deep enough into the spaces between the teeth that a first wall thickness of tissue, but not the second wall thickness thereof, protrudes into the needle passageway. Next, two needles attached to opposite ends of a length of bioabsorbable thread are forced completely through the passageways and the tissue, one needle for each passageway, thereby creating an encircling series of stitches in the wall of the tubular tissue. The needles are then detached from the thread and removed from the body, thereby leaving a purse string suture in the tubular tissue, ready to be drawn snug and tied.

Preferably, a novel clamping arrangement is operable from outside the patient's body to secure the jaws tightly together. The surgeon, working outside the wound, can then force the thread-carrying needles into the two passageways in the instrument by using forceps. Once the front ends of the needles protrude a sufficient distance beyond the ends of the jaws to expose the thread, the ends of the thread can be grasped by forceps through a second cannula, for example, and cut to release them from the needles. While holding the thread ends to prevent the ends from being pulled back out of the tissue, the needles can then be withdrawn from the instrument. After that the clamping mechanism can be released and the jaw can be swung fully open and the instrument withdrawn through the first cannula.

A preferred moving mechanism includes a positioning device for moving the first jaw between the insertion position and an intermediate position between the insertion and clamping positions, and a clamping device for applying a clamping force to the pair of jaws to move the first jaw to the clamping position.

Preferably the positioning device comprises a cable operable from outside the patient's body for pushing and pulling the first jaw about the first pivot axis between the insertion and intermediate positions.

It is preferred that the first jaw is connected to a support beam and the clamping device comprises a tube slidable along the main shaft and the support beam to generate the clamping force to the pair of jaws.

It is also preferred that the clamping device further includes a lever assembly mounted on a proximal end of the main shaft and operable outside the patient's body for selectively pushing or pulling the tube along the main shaft.

Preferably the surgical suturing instrument also includes a device for releasably locking the jaws together after they have been tightened against each other by operation of the clamping device, the locking device also being operable from outside the patient's body when the jaws are clamped across the section of tubular tissue inside the body.

It is also preferred that the first and second jaws are respectively rotatable about second and third pivot axes, which are orthogonal to the first pivot axis.

In still another aspect of the present invention, a suturing instrument is comprised of an elongated shaft; a pair of relatively movable jaws for clamping the tubular tissue therebetween, the first jaw being substantially pivotable with respect to the second jaw about a first pivot axis, and each jaw having a row of spaced-apart, uniform-size teeth; a mechanism for articulating the pair of jaws about a second pivot axis orthogonal to the first pivot axis; and a mechanism for closing the jaws together to clamp the tubular tissue therebetween. The tubular tissue is clamped by meshing the row of teeth of the first jaw with the row of teeth of the second jaw to bend the tissue therebetween into a wavelike configuration with the collapsed tube forming a two-wall thickness of tissue overlying the crest of each tooth. Each tooth is configured as discussed above so the needle threads the suturing material through only the wall of tissue that contacts the teeth through the which the needle passes, and does not sew the tube closed. By forcing two needles attached to opposite ends of a length of suturing thread material completely through passageways formed by the channels in each row of teeth in the tissue, an encircling series of stitches is created in the wall of the tubular tissue. Preferably, each needle can be snapped-off near the suture and the needle heads and suture can be withdrawn from the body through a cannula while the needle shafts are withdrawn back through the passageways. The jaws of the instrument can then be opened and the tissue released. The jaws are closed again to withdraw the suturing instrument through another cannula in the body. The ends of the suture are cut from the needle head and drawn snugly around an anastomosis ring or the like and knotted to form a purse string suture.

A preferred actuating mechanism includes a driving rod for pivoting the first and second jaws about the first pivot axis. The driving rod is preferably connected to one of the jaws through a lost motion lever for raising and lowering that jaw about a third pivot axis parallel to the first pivot axis. The first and third pivot axes are preferably offset from one another to increase the clamping force of the lost motion lever.

It is also preferred that the articulating mechanism includes a camming rod for abutting one of the jaws and pivoting the pair of jaws about the second pivot axis. The articulating mechanism also includes stop means for limiting the articulating movement of the jaws.

These and other objects, aspects, features, and advantages of the present invention will become apparent from the following detailed description of the preferred embodiments taken in conjunction with the drawings.

BRIEF DESCRIPTION OF THE DRAWINGS

FIG. 2 is an isometric view of the distal end (jaw end) of the purse string suturing instrument of the first embodiment in an open position;

FIG. 3 is an isometric view of the handle assembly of the suturing instrument of the first embodiment of the present invention;

FIG. 4 is a partial plan view of the handle assembly shown in FIG. 3;

FIG. 5 is a partial isometric view of a proximal end of one of the push rods of the suturing instrument of the first embodiment of the present invention;

FIG. 6 is a side elevational view of the distal end (jaw end) of the suturing instrument of the first embodiment of the present invention being moved toward a clamping position around a tubular tissue;

FIG. 7 is a side elevational view of the distal end of the suturing instrument of the first embodiment of the present invention in a position to be clamped;

FIG. 8 is a side elevational view of the distal end of the suturing instrument of the first embodiment of the present invention in a fully clamped position with the suturing needles inserted therethrough;

FIG. 9 is a cross-sectional view along lines 9—9 of FIG. 8;

FIG. 10 is a cross-sectional view along lines 10—10 of FIG. 8;

FIG. 11 is an enlarged side view of a suturing needle used in the present invention.

FIG. 33 is a side view of a suturing needle in accordance with the present invention;

FIGS. 33A through 33D are enlarged isolation views of the suturing needle in accordance with the present invention;

FIG. 34 is a side view showing one side of a handle for the suturing instrument of the third embodiment of the present invention in an open position; and FIG. 35 is a side view showing the opposite side of the handle of the third embodiment of the present invention in a closed position.

DETAILED DESCRIPTION OF THE PREFERRED EMBODIMENTS

FIGS. 1 through 12 depict a purse string suturing instrument in accordance with a first embodiment of the present invention.

Figure 1:
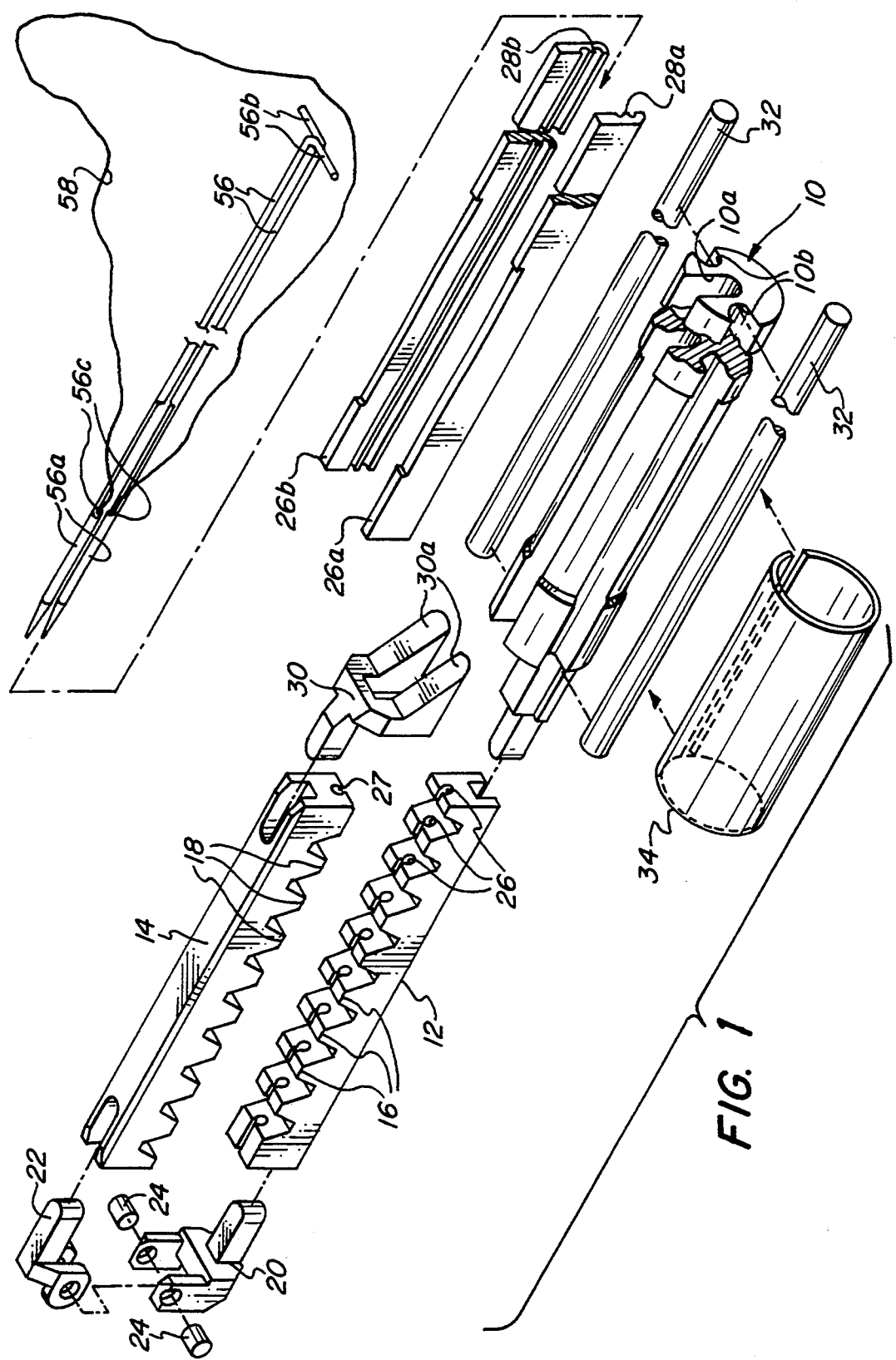
FIG. 1 is an exploded view of a major portion of the purse string suturing instrument in accordance with a first embodiment of the present invention.
Figure 12:
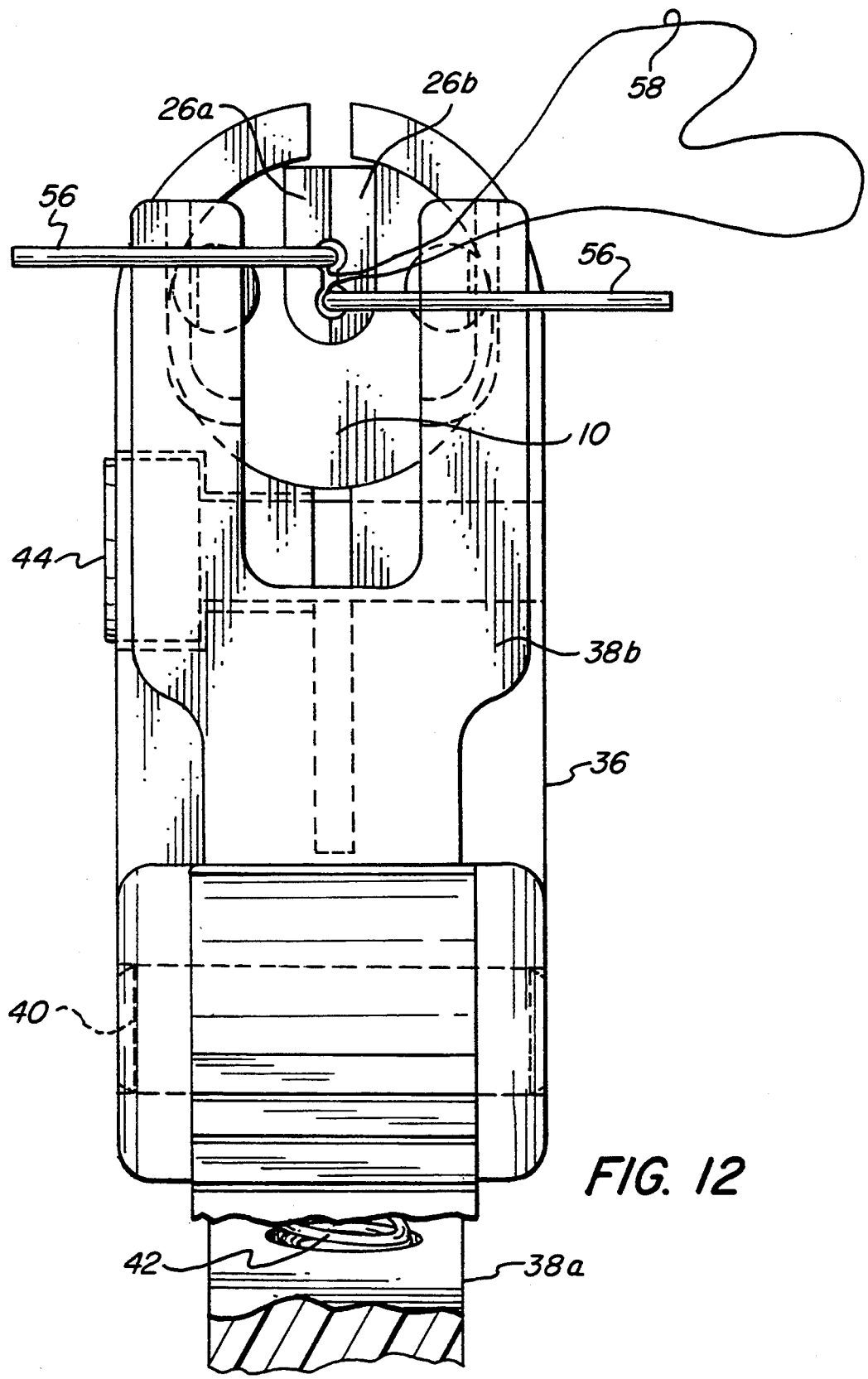
FIG. 12 is an elevational view of the proximal end of the suturing instrument of the present invention.

FIG. 1 illustrates a major portion of the purse string suturing instrument of the present invention. The instrument includes a main shaft 10, a lower jaw 12 and a complementary upper jaw 14. A proximal end of the lower jaw 12 is fixedly attached to a distal end of the main shaft 10. The jaws 12, 14 are designed to clamp a tubular tissue at a point where the purse string suture is to be placed. Hinge 20 is fixedly attached to a distal end of the lower jaw 12 and hinge 22 is fixedly attached to a hinge end of the upper jaw 14. Two relatively short pivot pins 24 are inserted into complementary appositioned holes of the hinges 20, 22 to establish a pivot axis. When mounted, the pins 24 are spaced apart along the direction of the pivot axis so that an empty space is provided between the pins. The upper and lower jaws are relatively moveable in a planar arc about the pivot axis between open and closed positions. In the open position the upper jaw is swung approximately 181 to 187 degrees, more preferably 184 degrees, from the closed position. The upper jaw 14 is prevented from swinging further by stops provided on the hinges 20, 22.

The lower jaw 12 is provided with a row of spaced-apart teeth 16 of uniform size and spacing. The upper jaw 14 is also provided with a complementary row of spaced-apart teeth 18. The teeth 18 are offset from the teeth 16 so that when the upper jaw is swung around the pivot point to the closed position opposed to the lower jaw, the teeth 16 can mesh with the teeth 18. (See FIGS. 6, 7 and 8.) A channel 26 is formed in the crest of each tooth 16 of the lower jaw 12. Each channel 26 runs parallel to the direction of the row of teeth. In cross-section, each channel is shaped like a keyhole including a circular portion at its bottom, i.e. the location most distant from the crest of the tooth in which the channel is formed, and a rectangular portion or slot extending from the circular portion to the crest of the tooth. The circular portions of channels of the row of teeth 16 are aligned so as to form a substantially straight passageway, which is segmented or interrupted by the gaps between the teeth. The teeth 18 of the upper jaw are formed with similar channels 27 to define a parallel passageway.

Needle guides 26a and 26b are positioned in a longitudinal slot 10a formed at the twelve o'clock position of the periphery of the main shaft 10. Each needle guide is formed of extruded plastic as an elongated member. A longitudinal groove 28a is formed on the inner surface of needle guide 26a. In cross-section, the groove 28a includes two spaced, semi-circular portions bridged by a straight portion. Needle guide 26b is formed as a mirror-image of guide 26a with a similar groove 28b. The guides 26a, 26b abut one another in the longitudinal slot of the main shaft 10 such that grooves 28a, 28b are positioned adjacent one another. In this manner grooves 28a, 28b combine to form a "dog-bone" passageway 31 (FIG. 9) having two circular conduits connected by a straight channel. As an alternative, the needle guides can be formed as a unitary extruded piece having a dog-bone passageway.

The needle guides 26a, 26b are mounted on the main shaft 10 with the lower halves of the guides being aligned with and abutting or near the lower jaw 12. The lower conduit of passageway 31 is aligned with the passageway defined by the channels 26 in the teeth of the lower jaw 12. When the upper jaw 14 is in the closed position, the upper halves of the guides 26a, 26b are aligned with the upper jaw and the upper conduit of the passageway 31 is aligned with the passageway defined by the channels 27 in the teeth of the upper jaw. The spacing of the upper and lower conduits of the passageway 31 may be slightly larger than the spacing between the channels 26 and 27 in the jaws when they are fully closed to ensure that the needles will enter the channels when jaws are slightly short of fully closed.

A bifurcated cam member 30 with two inclined plane cam ramps 30a is provided on an end of the upper jaw 14 opposite the hinged end. Each cam ramp 30a is engageable with a clamping end 32a of one of two pushrods 32. When the pushrods 32 are actuated and forced toward the cam member 30, the resultant force urges the upper jaw 14 downwardly in a further meshing engagement with the lower jaw 12. The pushrods 32 are slidable in elongated slots 10b provided at three and nine o'clock positions of the periphery of the main shaft 10.

After the needle guides 26a, 26b and the pushrods 32 are positioned in their respective slots, a spring band 34 made of sheet metal, for example, is snapped around the main shaft 10 to retain the guides and pushrods. The gap in the spring band is sufficiently small as not to permit any element from slipping out, regardless of the angular position of the gap.

The invention is not limited to the configurations described above. Many combinations of the aforementioned elements can be formed unitarily. For example, the upper jaw 14, hinge 22, and cam member 30 may be formed as one piece, as well as the main shaft 10, lower jaw 12 and hinge 20, or only the lower jaw 12 and hinge 20, etc.

As shown in FIGS. 2 and 3, the pushrods 32 are driven by a rotatable lever 38. The lever is rotatable relative to a handle 36 and pivotable about a pin 40 provided through the handle 36. The handle includes a grip portion 36a and a connection portion 36b. A hole is formed in the connection portion and the main shaft 10 is positioned therein. A screw 44 is then tightened to secure the handle 36 to the main shaft 10 with a clamping engagement. The lever 38 includes a grip portion 38a and a bifurcated U-shaped portion 38b bent at substantially a right angle with respect to the grip portion 38a. Each arm of the U-shaped portion 38b includes a slot on an inner side thereof to engage a notch 32b in a proximal end of a pushrod 32. See FIGS. 4 and 5. The notch can freely move along the length of the slot to accommodate the angular change of the U-shaped portion 38b through its full range of motion.

The lever 38 is biased away from the handle 36 by a spring 42, thereby normally retracting the pushrods 32. With this arrangement a user can grip the handle 36 and squeeze the lever 38 with one hand. Thus, a user can effectively control the clamping pressure between the lower jaw 12 and the upper jaw 14 with one hand.

A rigid locking mechanism 46 having ratchet teeth is provided on the proximal end of the handle 36. A rotatable locking mechanism 48 with complementary ratchet teeth is provided on the proximal end of the lever 38. As the lever 38 is squeezed toward the handle 36, the teeth of the rotatable locking mechanism 48 progressively mesh with the teeth of the rigid locking mechanism 48, thereby locking the relative positions of the handle 36 and lever 38. The rotatable locking mechanism 48 is rotated out of engagement with the rigid locking mechanism 46 to unlock the handle and lever in order to retract the pushrods 32.

Each end of a single length of bioabsorbable, monofilament suture or thread 58 is attached to a tip end 56a of a needle 56. The diameter of the needle is small enough to be slidable through the circular conduits in the needle guides 26a, 26b and the circular passageways of the teeth, yet large enough to prevent slipping from the circular conduits and passageways. A notch 56c can be formed where the tip end 56a meets the main body of the needle 56 to enable the tip end to be snapped off. The proximal end 56b of each needle is bent at a right angle to receive a pressing or pulling force. The suture 58 is of a diameter smaller than the width of the slot of the channels 26, 27 of the teeth and the width of the straight channel of the dog-bone passageway 30.

The procedure of forming a purse string suture in a tubular tissue using the suturing instrument of the present invention will be described in detail below.

Initially, the pursing string suturing device of the invention may be inserted through a small cannula 54 inserted in an abdominal wall 52 for example. The diameter of the cannula 54 is on the order of 12 mm, for example, and is sized so that, when in the open position, the lower jaw 12 and the upper jaw 14 can inserted therein. However, the cannula is too small to permit entry of the jaws when they are in the closed position. The cannula is also sufficiently large to permit insertion of the main shaft 10 up to its connection with the handle 36. Thus, only a small opening in the body is needed to insert the instrument.

Referring to FIG. 2, the distal end of the suturing instrument, with the jaws in the open position, is inserted in the cannula 54 in the vicinity of the tubular tissue to be sutured. In the open position the leading upper jaw 14 is at an angle, 184 degrees for example, relative to the lower jaw 12. Therefore, the upper jaw 14 including the cam member 30 are inserted at an angle. This permits the cam member 30 to be formed with a greater height, which presents a larger profile to be captured by the camming ends of the pushrods 32. Also, the jaws are less likely to inadvertently jackknife to the closed position when inserted at that angle since they are limit-stopped at that angle.

When the distal end of the suturing instrument is fully inserted, the lower jaw 12 is positioned below and transverse to the of the tubular tissue so to be sutured, as shown in FIG. 6. Forceps 57 are inserted through a second cannula (unshown) to grasp the upper jaw 14 and rotate it toward the closed position with the tubular tissue positioned between the jaws. The forceps 57 are then used to press the cam member 30 downwardly to align its cam ramps 30a with the camming surface 32a of the push rods 32, as shown in FIG. 7. When in alignment, the lever 38 is squeezed to force the pushrods 32 forwardly. As the pushrods advance, the camming surface 32a contacts the cam ramps 30a to force the cam member 30 and the upper jaw 14 downwardly, as shown in FIG. 8. Thus, the tubular tissue 50 is clamped between the upper and lower jaws with a desired degree of force, which is maintained by the interlocking of the teeth of locking mechanisms 46, 48.

As the jaws clamp the tubular tissue with the desired degree of force, the opposing rows of teeth 16, 18 bend the tissue 50 between them into a wavelike configuration. As depicted in FIG. 8, because the tube of tissue 50 is collapsed, a two-wall thickness of the tissue overlies the crest of each tooth.

At this time the needles 56, each of which are attached to an end of a suture 58, are inserted into the circular conduits of the passageway 30 defined by the needle guides 26a, 26b and through the passageways defined by the channels 26, 27 formed in the teeth 16, 18 of the jaws 12, 14. As each needle travels from tooth to tooth of one jaw, it pierces the wall of tissue that contacts that wall without penetrating the wall of tissue that contacts the other jaw. In this manner, each needle threads the suture through one wall of the two-wall thickness of the tissue and does not sew the tube closed. As the ends of the suture advance through the conduits and passageways, the connecting loop of the suture is free to pass through the slot of the dog-bone passageway 30. The hinge pins 24 do not interfere with the advancement of the needles because the needles pass between the pins 24. After the tip end 56a of each needle, including an end of the suture 58, emerges from the distal end of the jaws, an encircling series of stitches will have been formed in the wall of the tubular tissue.

If the needles 56 are provided with a frangible notch 56c, each tip end 56a can be snapped off with forceps manipulated through the second cannula. The remaining portions of the needles are then withdrawn back through the passageways. The tissue may be cut on one or the other side of the closed jaws. Thereafter the locking mechanism released, the upper jaw is swung to the open position, and the suturing instrument is removed through the first cannula 54. As the jaws are removed from the tubular tissue, the stitches are free to pass through the slots of the channels 26, 27 formed in the teeth. Afterward, the end of the tubular tissue can be placed over an anastomosis ring or the like and the purse string suture is then drawn snugly over the ring and tied in a conventional manner.

If the needles are not frangible, the needles are first withdrawn slightly to create a loop in each end of the suture. These loops are snipped and the free ends of the suture are grasped with forceps. Then the entire needles are withdrawn and the suturing instrument is removed in the same manner as above.

FIGS. 13 through 26 depict a purse string suturing instrument in accordance with a second embodiment of the present invention.

Figure 13:
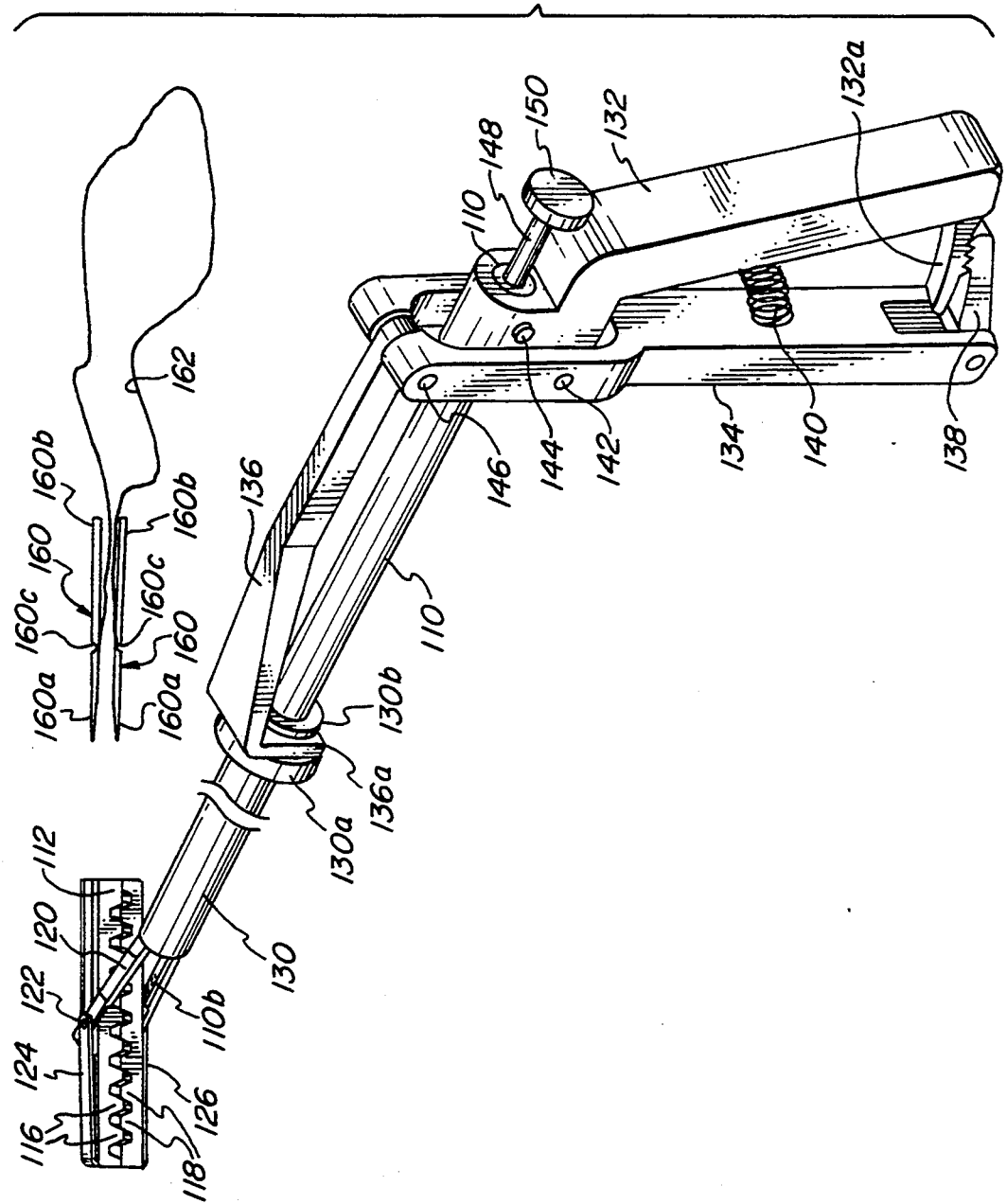
FIG. 13 is an isometric view of the purse string suturing instrument in accordance with a second embodiment of the present invention.
Figure 14:
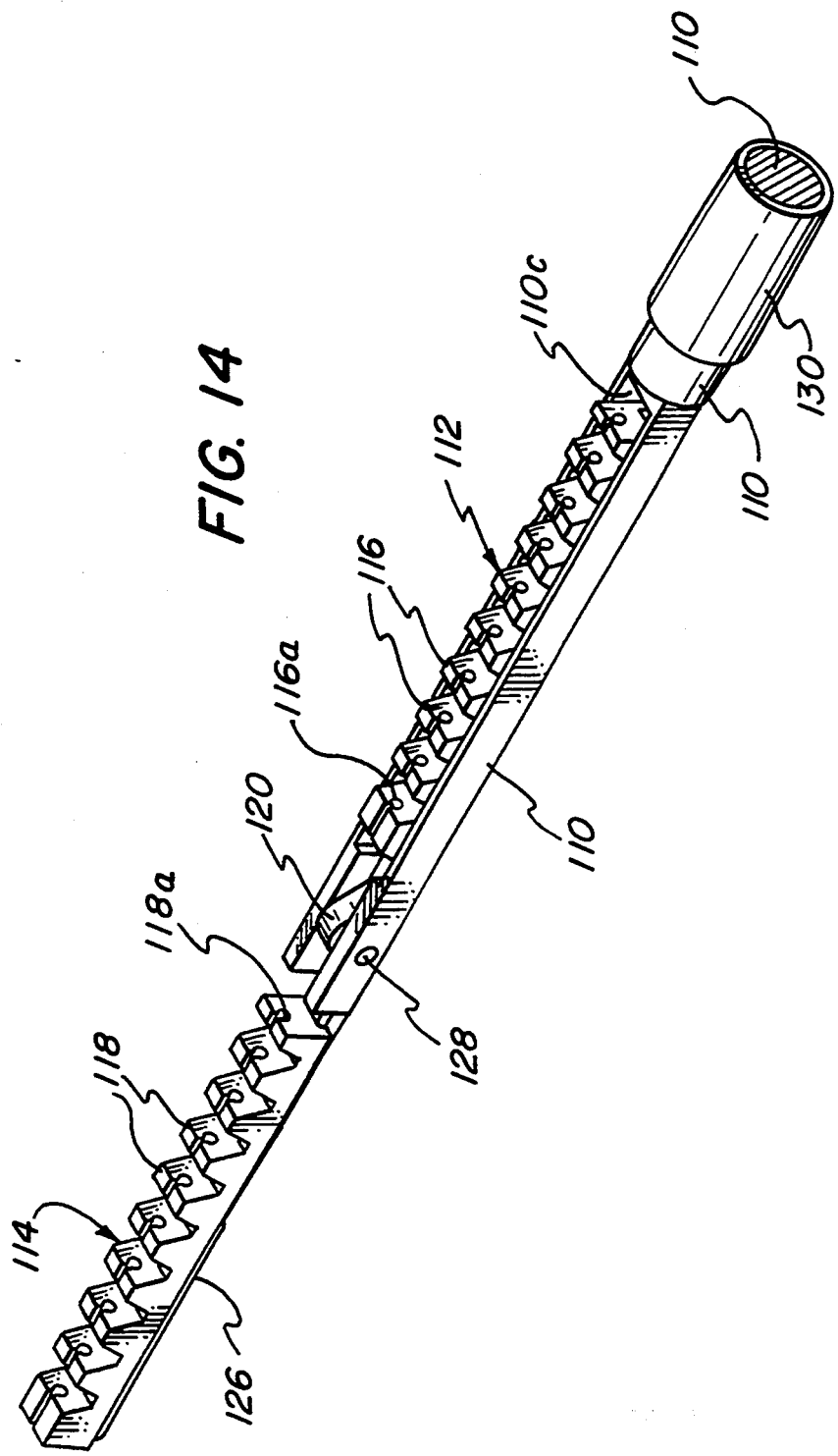
FIG. 14 is an isometric view of the distal end (jaw end) of the purse string suturing instrument of the second embodiment of the present invention in an insertion (open) position.
Figure 15:
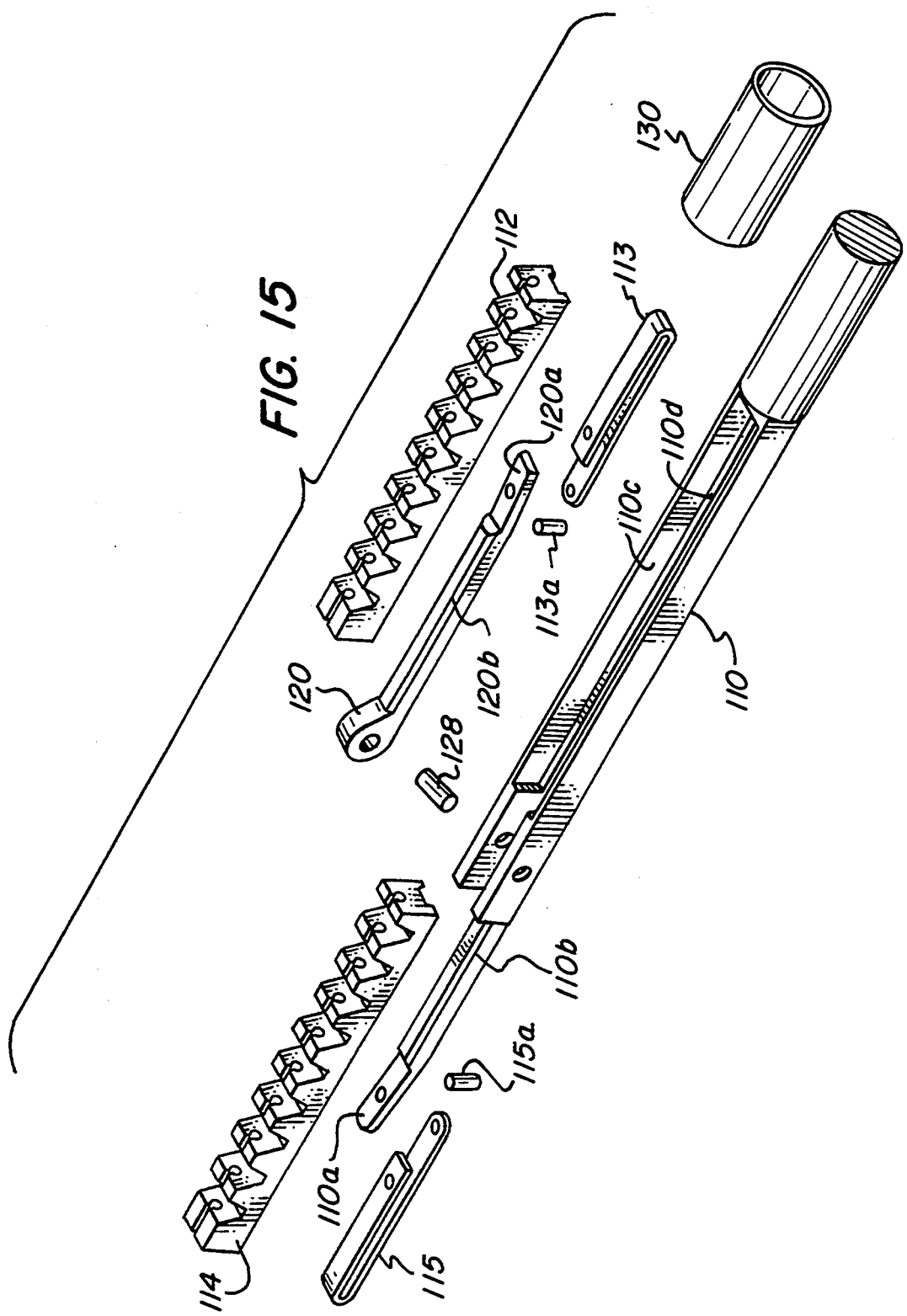
FIG. 15 is an exploded view of the distal end of the suturing instrument of the second embodiment of the present invention.
Figure 16:
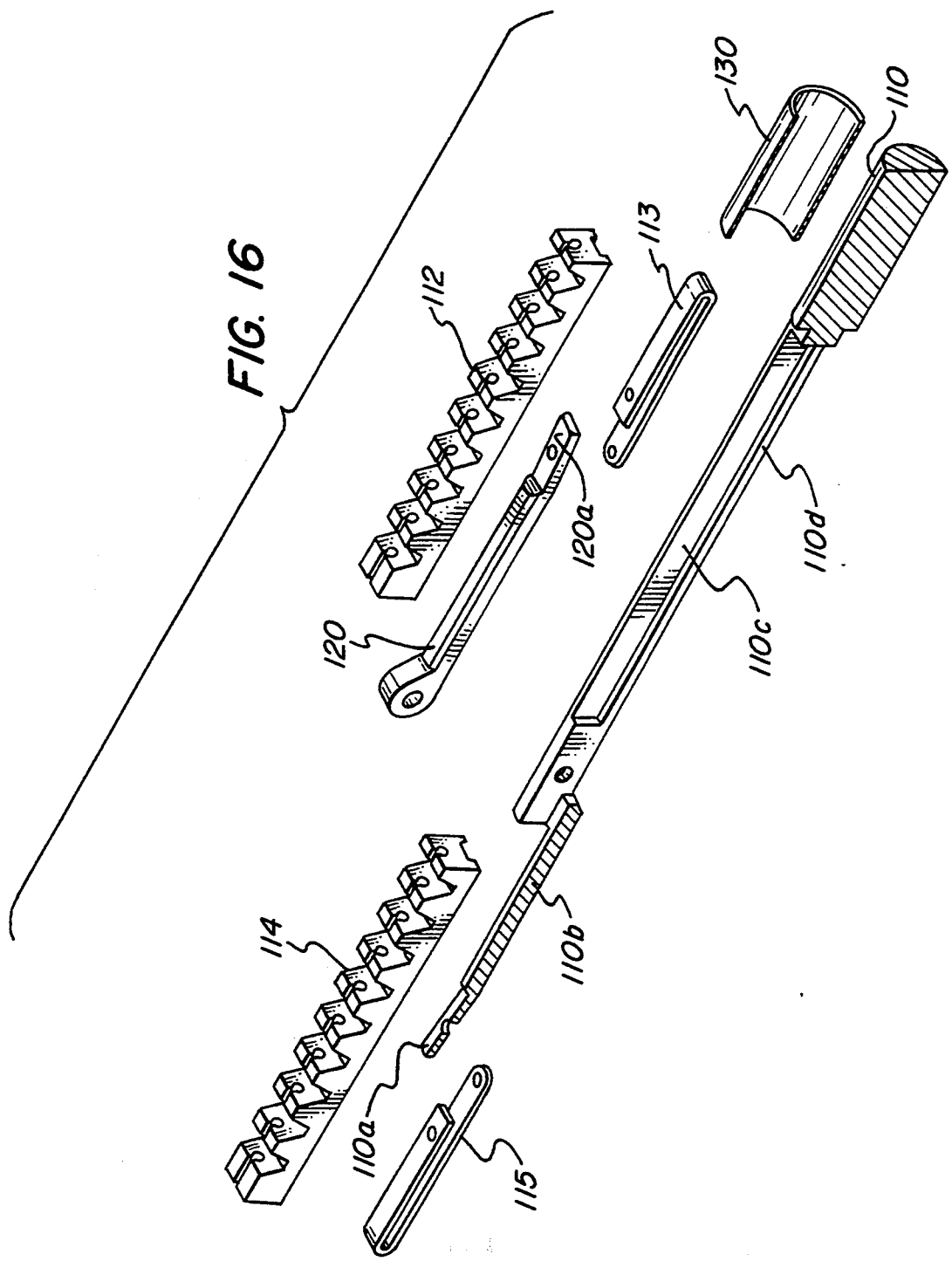
FIG. 16 is an exploded partial vertical cross-sectional view of the distal end of the suturing instrument of the second embodiment of the present invention.
Figure 17:
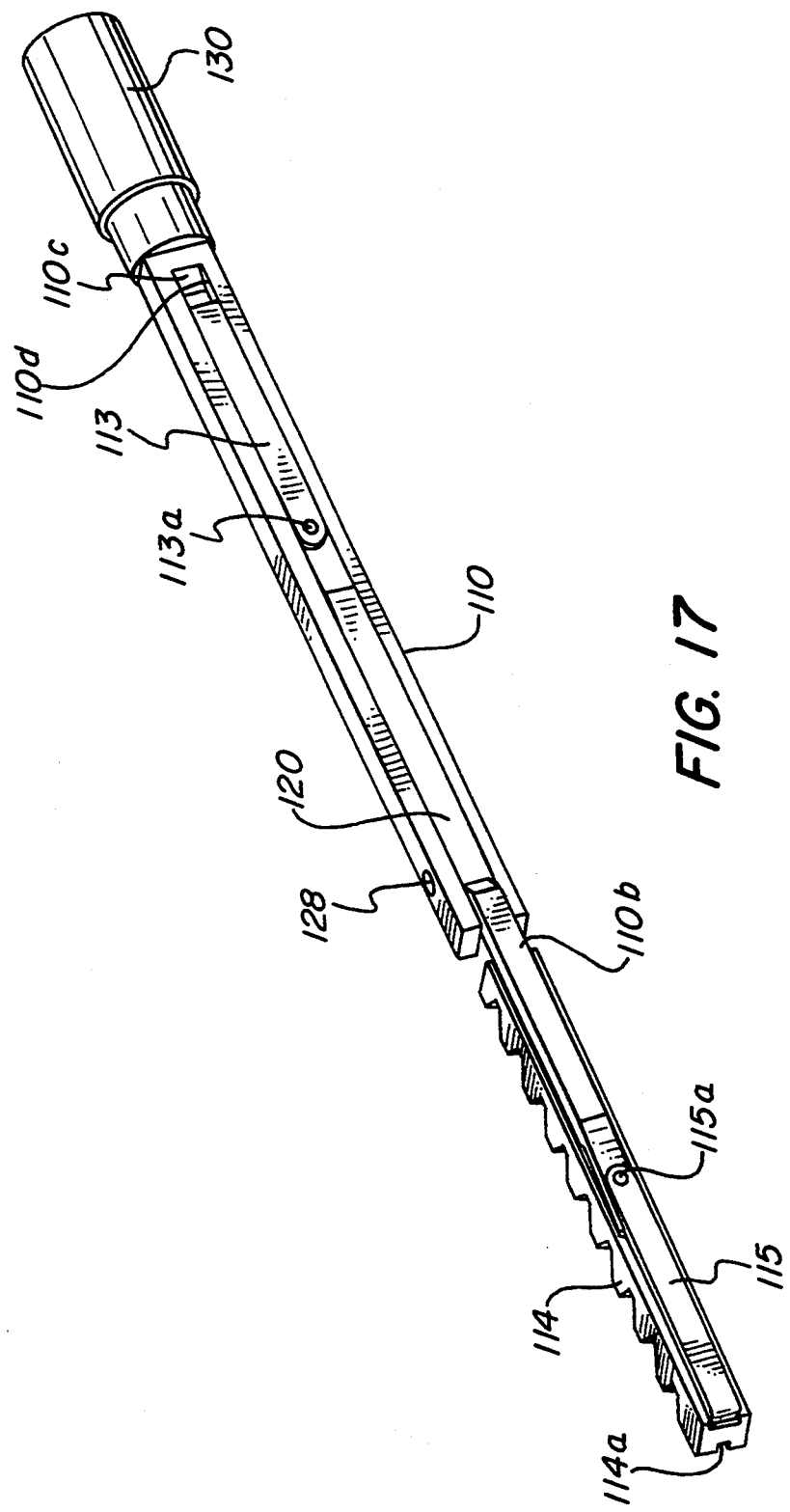
FIG. 17 is an isometric view of the bottom of the distal end of the suturing instrument of the second embodiment of the present invention.

FIG. 13 illustrates a major portion of the purse string suturing instrument of the present invention. The instrument includes a main shaft 110, a first jaw 112 and a complementary second jaw 114. The first jaw 112 is connected to the main shaft 110 through a support beam 120, which is pivotable about a pivot axis 128 in the main shaft as shown in FIG. 14. The second jaw 114 is fixedly attached to support beam 110b, which is integrally formed on a distal end of the main shaft 110 also shown in FIG. 14. The jaws 112, 114 are designed to clamp a tubular tissue at a point where the purse string suture is to be placed.

As is clear in FIG. 14, the first jaw 112 is provided with a row of spaced-apart teeth 116 of uniform size and spacing. The second jaw 114 is also provided with a complementary row of spaced-apart teeth 118. The teeth 118 are offset from the teeth 116 so that when the first jaw is swung around the pivot axis 128 to the clamping (closed) position opposed to the second jaw, the teeth 116 can mesh with the teeth 118. A channel 116a is formed in the crest of each tooth 116 of the first jaw 112. Each channel 116a runs parallel to the direction of the row of teeth. In cross-section, each channel is shaped like a keyhole including a circular portion at its base, i.e. the location most distant from the crest of the tooth in which the channel is formed, and a rectangular portion or slot extending from the circular portion to the crest of the tooth. The circular portions of channels of the row of teeth 116 are aligned so as to form a substantially straight passageway, which is segmented or interrupted by the gaps between the teeth. The teeth 118 of the second jaw are formed with similar channels 118a to define a parallel passageway.

Each end of a single length of bioabsorbable, monofilament suture or thread 162 is attached to a tip end 160a of a needle 160 as shown in FIG. 13. The diameter of the needle is small enough to be slidable through the circular passageways of the channels 116a, 118a of the teeth, yet large enough to prevent slipping from the passageways. A notch 160c can be formed where the tip end 160a meets the main body of the needle 160 to enable the tip end to be snapped off. The suture 162 is of a diameter smaller than the width of the slot of the channels 116a, 118a of the teeth.

Referring now to FIGS. 14 through 19, each jaw is pivotally mounted to its respective support beam 120, 110b about a pin 113a, 115a and is held against the support beam via a hairpin-shaped leaf spring 113, 115 which specifically holds the jaw against a flat section 120a, 110a of each beam.

In FIG. 13, the jaws are shown in a closed (clamping) position. The jaws are pressed closed by the action of the sleeve 130 riding over the jaw support beams 110b, 120. The sleeve 130 is a slide tube which can be moved distally along the shaft 110 to a position where it can effect a camming action between the two jaw support beams 110b, 120, which results in squeezing the jaws 112, 114 together. Alternately, it can be moved proximally along the shaft to expose a nesting area 110c when retracting the jaw and beam assembly. An enlarged flange area 130a near the end of the sleeve contains an air sealing diaphragm (not shown) secured inside as an integral part of the proximal end of the sleeve. A groove 130b in the flange area of the sleeve is provided to engage a forked end 136a of a pusher 136. There is enough clearance between the groove 130b and the forked end 136a of the pusher 136 so that the pusher can move its pivoted end, at the pin 146, toward or away from the shaft 110 a reasonable amount without the fork binding in the groove. The diaphragm mentioned above provides an air seal against the shaft 110. The cannula into which the suturing instrument is inserted should also be provided with a diaphragm, which will wipe against the sleeve 130 as an air seal. This will prevent leakage from the pressurized abdominal area during the suturing operation.

Referring once again to FIG. 13, a handle 132 is affixed to the proximal end of the main shaft 110 by a pin 144 or a clamp, for example. A lever 134 is pivotally mounted on the handle via a pin 142. The lever 134 is connected by the pin 146 to the pusher 136 and is biased open with a spring 140 until the lever reaches a limit stop, namely the handle mounting pin 144, in the stationary handle 132, thereby normally retracting tube 130 via pusher 136. With this arrangement a user can grip the handle 132 and squeeze the lever 134 with one hand. Thus, a user can effectively control the clamping pressure between the first jaw 112 and the second jaw 114 with one hand.

A rigid locking mechanism 132a having ratchet teeth is provided on the proximal end of the handle 132. A rotatable locking mechanism 138 with complementary ratchet teeth is provided on the proximal end of the lever 134. As the lever 134 is squeezed toward the handle 132, the teeth of the rotatable locking mechanism 138 progressively mesh with the teeth of the rigid locking mechanism 132a, thereby locking the relative positions of the handle 132 and lever 134. The rotatable locking mechanism 138 is rotated out of engagement with the rigid locking mechanism 132a to unlock the handle and lever in order to retract the pusher 136 and the tube 130.

The forked pusher 136 is pivotally mounted to the top of the lever 134 so that squeezing the lever toward the handle 132 drives the sleeve 130 to the previously mentioned camming position on the jaw support beams 110b, 120. The fork end 136a of the pusher fits into the groove 130b on the proximal end of the sleeve 130, so that the sleeve is driven in either direction which the motion of the lever 112 dictates. The forked end 136a of the pusher can be swung up out of engagement with the groove 130b on the end of the sleeve 130 so that the sleeve can be moved a long distance toward the proximal end of the tool as needed as when nesting the jaw, as shown in FIG. 14.

A rugged push-pull rod 148 extends through the center of the shaft 110. The push-pull rod 148 has a knob 150 on its proximal end with which it can be actuated by the user. The push-pull rod is connected to a cable 148a inside the shaft as shown particularly in FIG. 20. The purpose of this cable is to rotate the support beam 120 along with the jaw 112 which the beam supports, for positioning the support beam at an intermediate position to be cammed by the sleeve 130, and also to cause retraction of that assembly back into the nesting area 110c in the shaft 110 after the purse string suturing operation, once the sleeve 130 has been retracted sufficiently so that it is not obstructing the nesting area.

In FIG. 14, the pivotable support beam 120 and the jaw 112 which it carries are swung about pin 128 into the nesting area 110c in the shaft 110. The jaws remain in this position while being inserted and removed through a cannula (not shown). The sleeve 130 is shown in its most retracted (proximal) position where it resides when the jaw 112 is nested as shown. Due to the size required of the jaws for strength and the small inside diameter of the cannula to be used, the sleeve 130 is not designed to fit over the jaw 112, but it is designed to fit through the cannula. The most distal jaw 114 is on the end of the non-rotating support beam 110b, as this beam is part of the main shaft 110. In this condition the jaws and their support beams can be inserted through a relatively small diameter cannula. Once the most proximal jaw 112 (the last one through the cannula) has cleared the cannula, it along with its support beam 120 may be swung out of the recess or nest 110c and pivoted about the pin 128 by depressing the knob 150 to advance the cable 148a as will be described further below. The pin 128 has a transverse axis through the shaft 110 and the support beam 120 so that the jaw 112 can be rotated. Rotation occurs until the support beam and jaws 112 come around toward the other jaw 114 and make contact with it or come close to it.

Referring again to FIGS. 15, 16, 17 and 18, it should be noted that the shaft 110 is an integrated element encompassing a cylindrical body at the proximal end, the jaw support beam 110b at the distal end, and a nesting section having recess 110c for some distance in the middle where the jaw 112 and the support beam 120 can be sufficiently retracted and nested on the imaginary centerline of the instrument, so that the assembly can fit through a small diameter cannula. It should also be noted that the recess 110c cuts completely through the shaft 110 so that a blind pocket is not formed and, therefore, material cannot rest in this nesting area and block the swing of the jaw/beam assembly back into this nesting area prior to the removal of the instrument back through the cannula. A shelf 110d in the recess 110c acts as a limit stop for jaw 112 when it is retracted into the recess 110c. This assures that the jaw will be nested at a position which presents the smallest overall diameter. The outside surfaces of the shaft 110 along the area of the recess 110c are shown flat for convenience in these drawings, but could actually be an extension of the same cylindrical shaft as far as the pivot pin 128, interrupted as needed by the cutout areas 110c and 110d.

Figure 19:
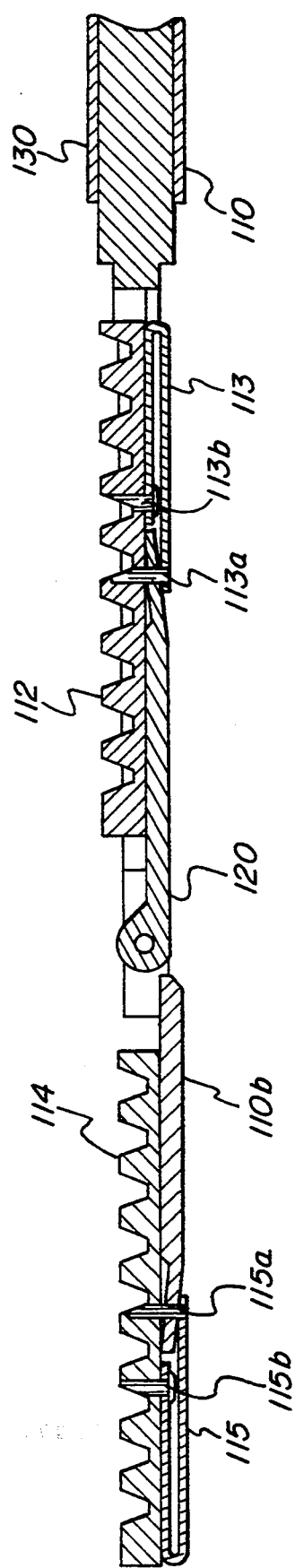
FIG. 19 is a vertical cross-sectional view of the distal end of the suturing instrument of the second embodiment of the present invention.

Referring to FIG. 19, the hairpin springs 113, 115 holding the jaws 112, 114 against the support beams 110b, 120 are shown. The hairpin springs are secured permanently to their respective jaws by rivets 113b, 115b. The hairpin springs are formed in a shape that normally returns to a position closed more than that shown, if unrestricted, and in this manner they provide a spring load biasing force against the support beams at all times. Pivot pins 113a, 115a are secured permanently in their respective jaws, and protrude out far enough out so that, as the jaws rotate relative to their support beams a detent displacement is overcome and there is no risk of the support beams slipping off of the end of the pin. Each hairpin spring employs a clearance hole about its pivot pin but does not use the pin to establish its location. Therefore, each hairpin spring can be deflected completely off the end of a pivot pin and continue applying force against the support beam. The pivot pins 113a and 115a must be restricted to a reasonable length, as they just fit through the cannula along with the rest of the assembly.

Figure 18:
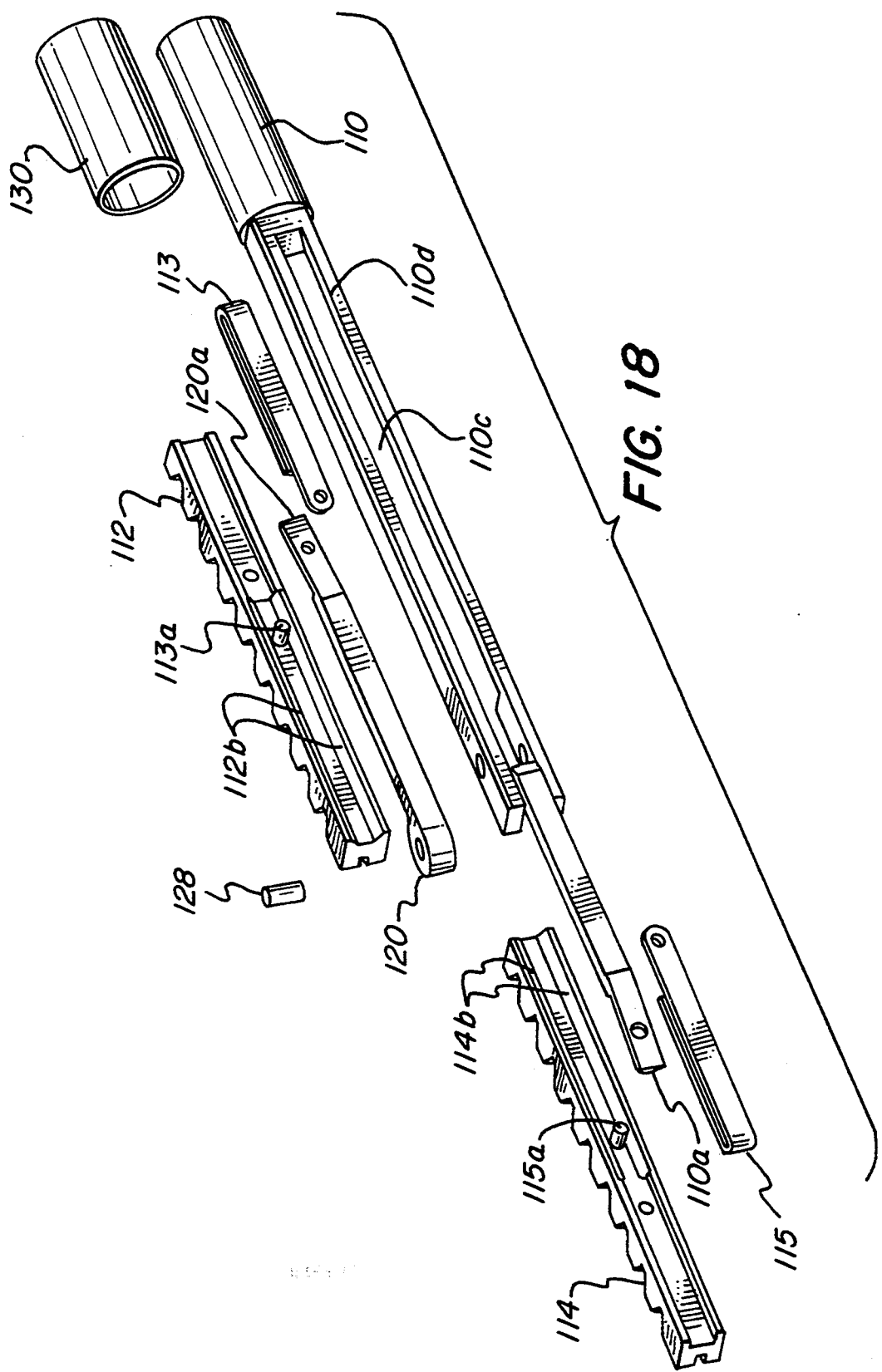
FIG. 18 is exploded view of the bottom of the distal end of the suturing instrument of the second embodiment of the present invention.

As can be seen in FIG. 18, the underside of each jaw includes angled walls 112b, 114b, which line a detent channel. During insertion, the jaws are positioned parallel to their respective support beam since each support beam is held in the detent channel by the force of the hairpin spring. In order to move the jaws to the operational position, an external force can be applied to each jaw to overcome the detent force and rotate the jaw at an angle relative to its respective support beam. The force of the springs will then hold the flat ridges on the underside of each jaw flush against the flats 110a, 120a of the support beams.

Figure 20:
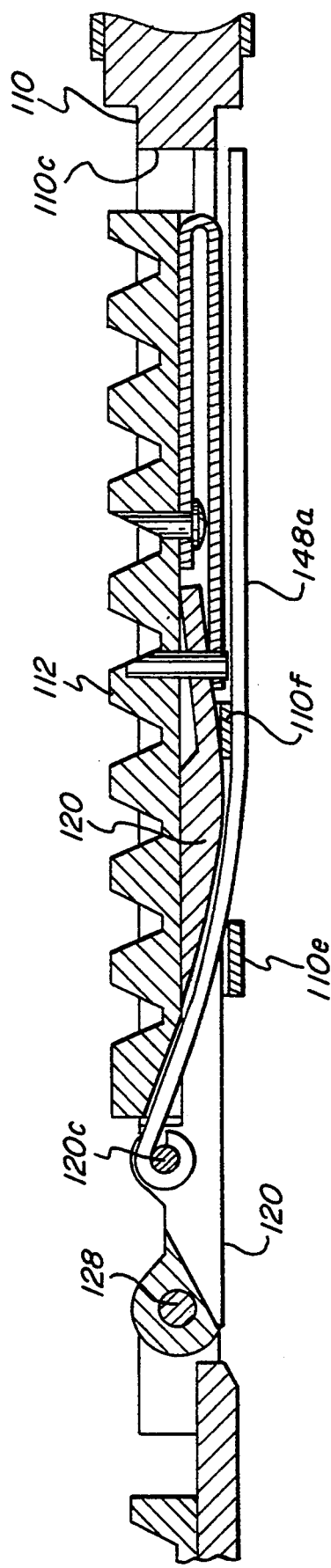
FIG. 20 is an enlarged vertical cross-sectional view of the pivot portion of the distal end of the suturing instrument of the second embodiment of the present invention.

Referring now to FIG. 20, cable 148a is shown as a flexible member attached to a pin 120c mounted on the rotatable support beam 120. This pin 120c is positioned in relation to the pivot pin 128 so that a pushing or pulling action imparted by the cable against pin 120c can cause rotation of support beam 120 about pivot pin 128 along with the jaw 112. In this manner, the beam and jaw assembly can be remotely swung into or out of the nesting area in the shaft 110. The cable 148a travels along or through the shaft until it is joined to the push-pull rod 148. In order to cause the cable to respond and flex properly as it experiences applied axial force, it is necessary to provide strategically located vertical restraints to keep the cable from buckling and to cause it to provide force in the proper direction to the pin 120. The restraints are typically in the form of bridges 110e, 110f, which bridge the shaft 110 at the bottom of the jaw nesting recess 110c.

The procedure of forming a purse string suture in a tubular tissue using the suturing instrument of the present invention will be described in detail below. Initially, the purse string suturing device of the invention may be inserted through a small cannula inserted in an abdominal wall, for example. The diameter of the cannula (not shown) is on the order of 10 mm, for example, and is sized so that, when the suturing device is in the insertion (open) position, the first jaw 112 and the second jaw 114 can be inserted therein. However, the cannula is too small to permit entry of the jaws when they are in the clamping (closed) position. The cannula is also sufficiently large to permit insertion of the main shaft 110 including the sleeve 130 up to the enlarged flange area 130a. Thus, only a small opening in the body is needed to insert the instrument.

The distal end of the suturing instrument, with the jaws in the open position, is inserted in the cannula in the vicinity of the tubular tissue to be sutured. In the open position the leading jaw 114 is at an angle, substantially 180 degrees, relative to the jaw 112.

Figure 21:
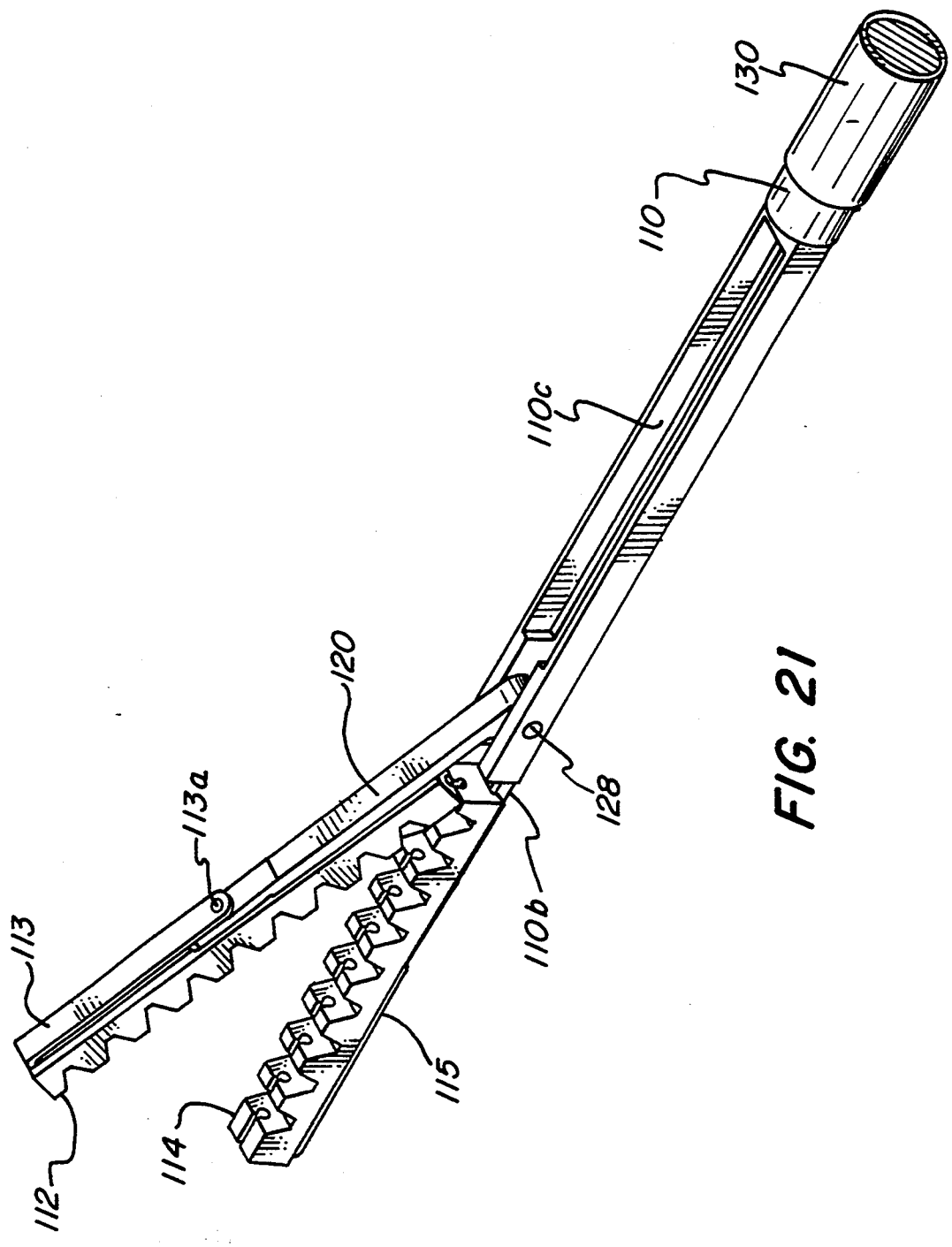
FIG. 21 is an isometric view of the distal end of the suturing instrument of the second embodiment of the present invention with the jaws in an intermediate position.

When the tool is sufficiently inserted through the cannula so that the most proximal jaw 112 (the last one through the cannula) has cleared the cannula, the knob 150 is pushed by an operator, which causes the beam 120 and jaw 112 assembly to rotate from its most proximal (insertion) position to a more distal (intermediate) position toward the other jaw 114 as shown in FIG. 21. The assembly pivots about the pin 128, which has a transverse axis through the shaft 110 and the support beam 120.

Figure 22:
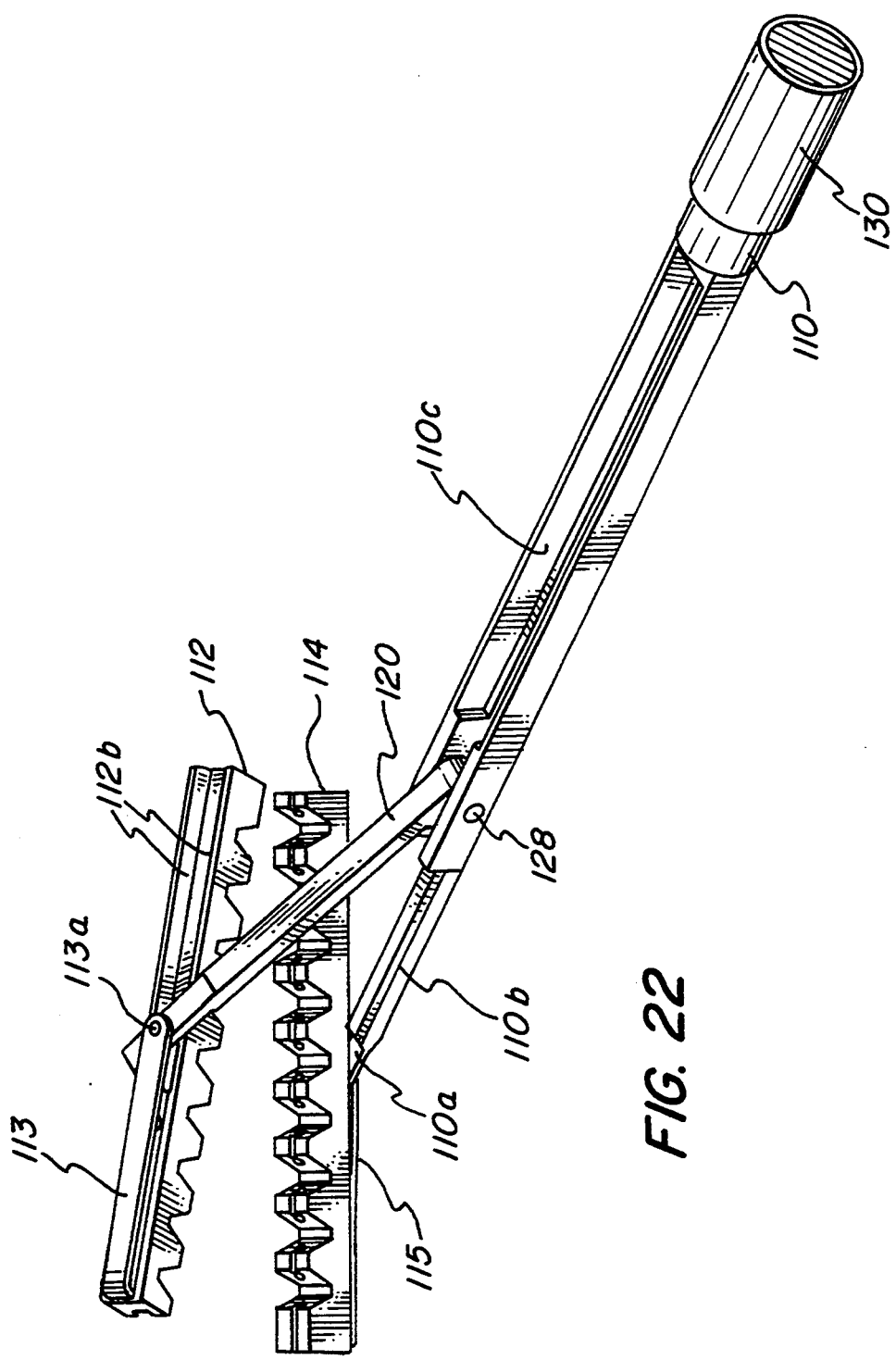
FIG. 22 is an isometric view of the distal end of the suturing instrument of the second embodiment of the present invention with the jaws rotated to an operational position.
Figure 23:
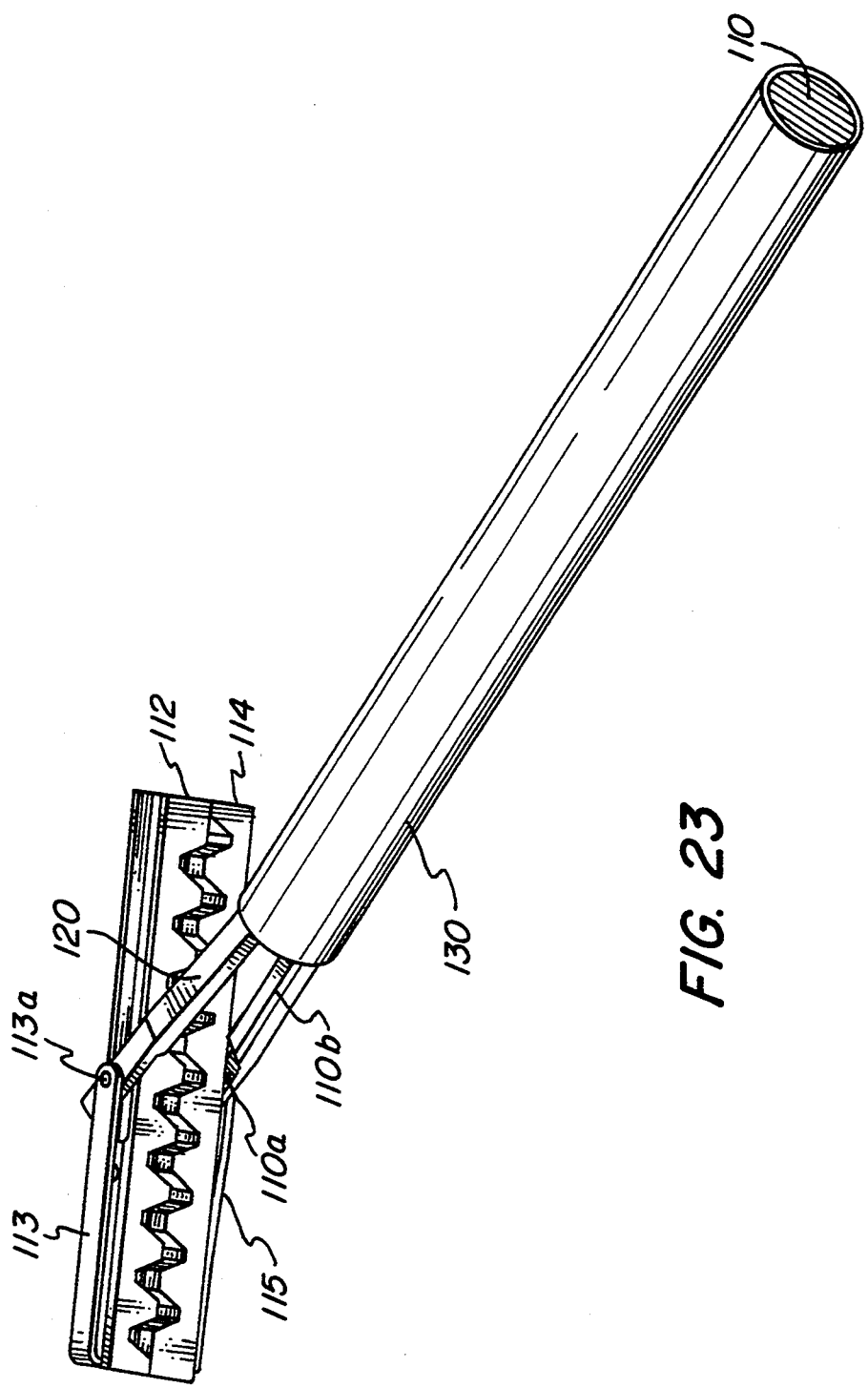
FIG. 23 is an isometric view of the distal end of the suturing instrument of the second embodiment of the present invention with the jaws in a clamping position.
Figure 24:
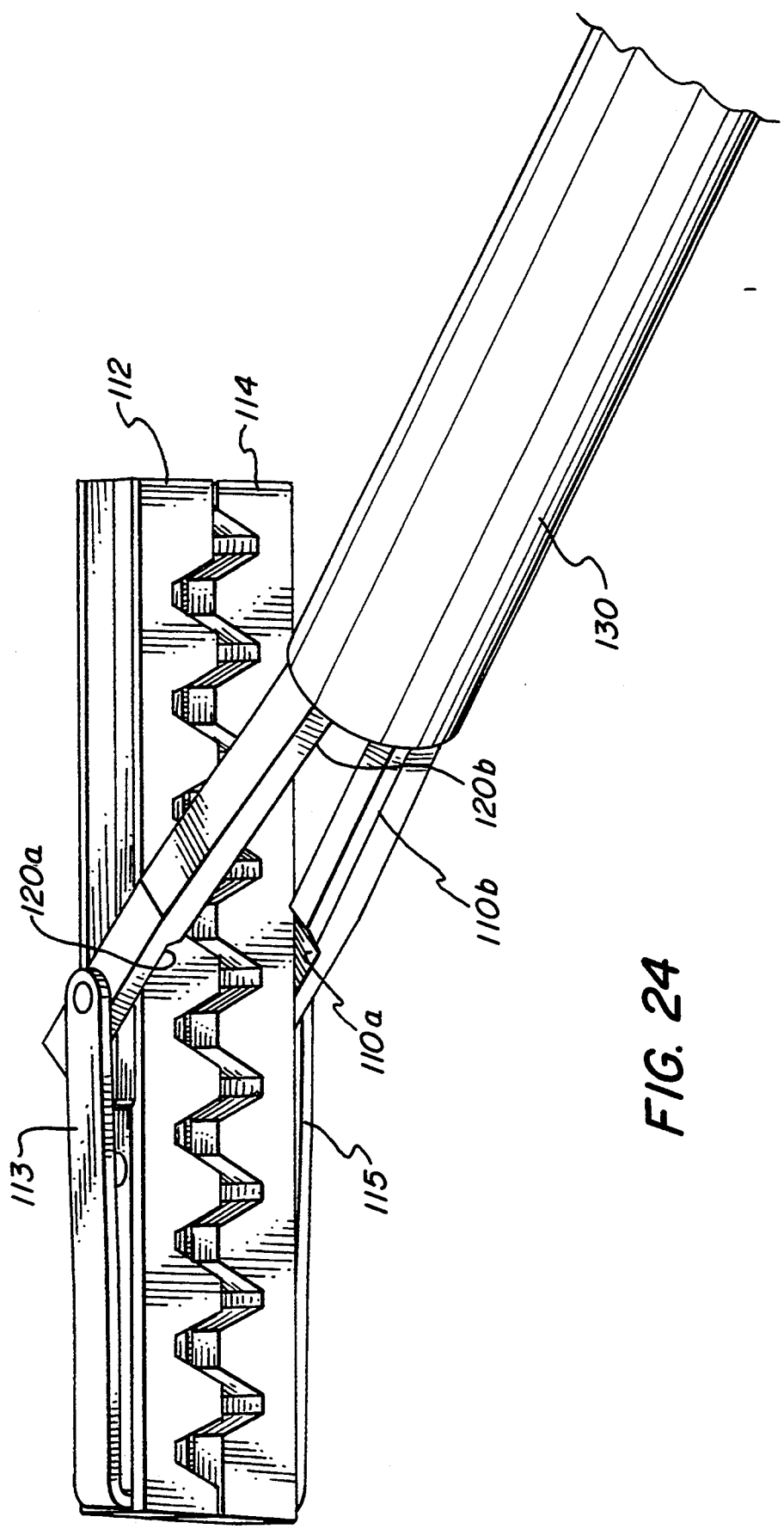
FIG. 24 is an enlarged isometric view of the distal end of the suturing instrument of the second embodiment of the present invention with the jaws in the clamping position.
Figure 25:
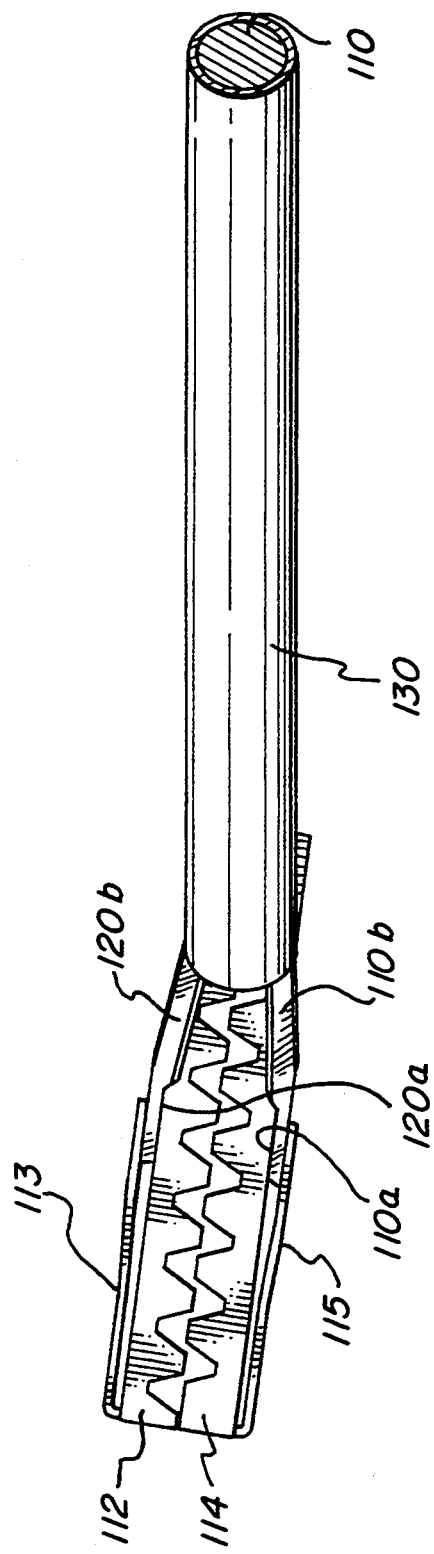
FIG. 25 is another isometric view of the distal end of the suturing instrument of the second embodiment of the present invention with the jaws in the clamping position.
Figure 26:
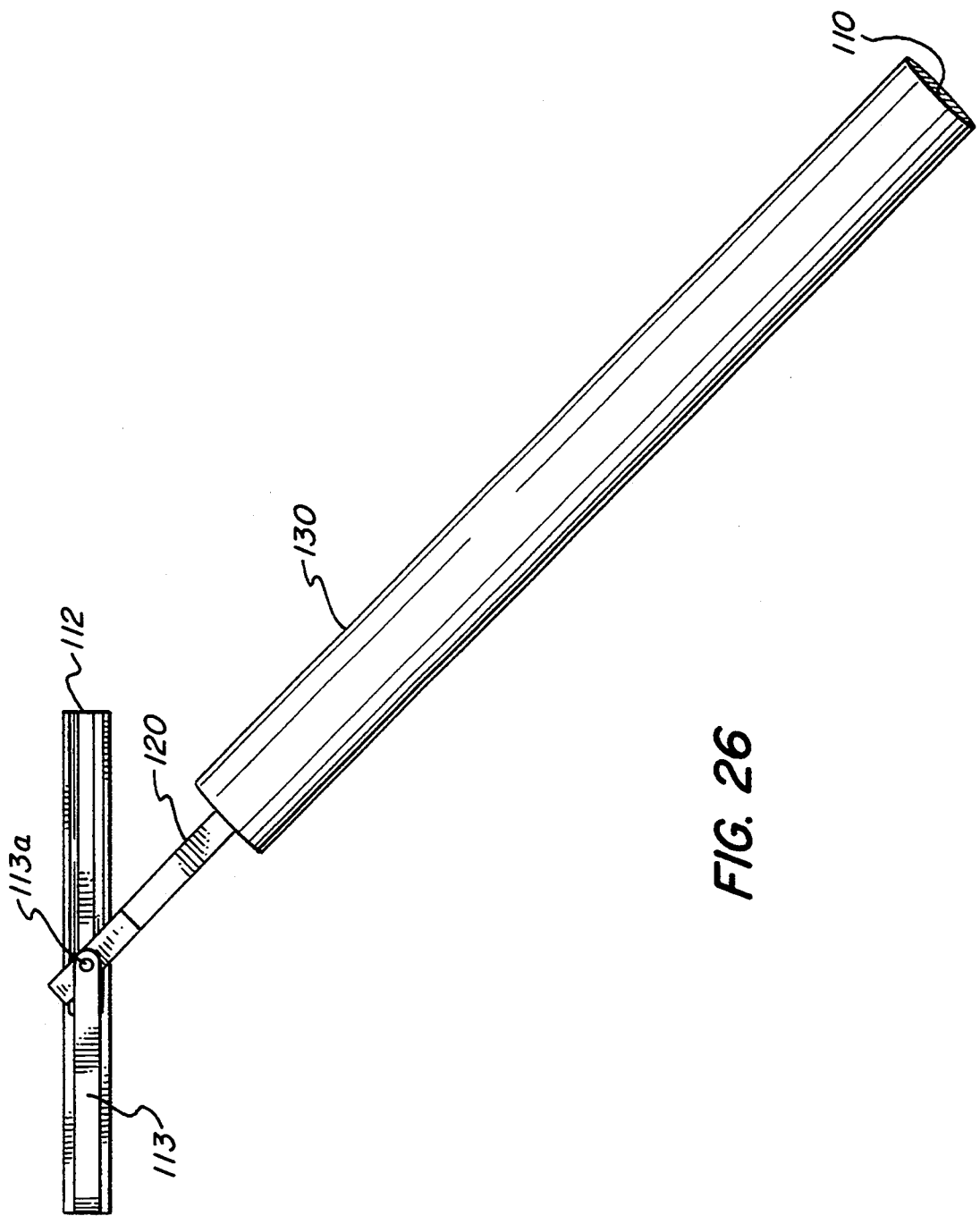
FIG. 26 is a plan view of the distal end of the suturing instrument of the second embodiment of the present invention with the jaws rotated in the clamping position.

At this time, and referring to FIG. 22, the jaws 112 and 114 must be gripped by use of any other separately introduced tool, such as forceps of a probe (not shown), and cocked outwardly to the side so that they each snap out of their spring loaded detent positions over angled edges, which maintained them centered on their beams 110b, 120. Both jaws are cocked in the same direction and angle. The force provided by the hairpin springs now holds the angled flats on the ends of the support beam ends 110a and 120a against the plane presented by the two back most ridge tops of each jaw.

Referring to FIGS. 23, 24, 25 and 26, the jaws 112, 114, which are now each cocked at an angle to the shaft 110, typically 45 degrees, are in an operational or ready position to complete clamping.

The tool is positioned so that the jaws 112, 114 are cocked and located as desired over the tissue (not shown) to be sutured. Then the sleeve 130 is slid by hand down over the shaft 110 and continues sliding until it comes to rest against the support beams 110b, 120. The sleeve had previously been located at its most proximal position up the shaft, with its distal end just clear of the previously nested jaw 112. When moved to this position by pushing with the hand, the sleeve had to overcome only the friction of the two air sealing rubber diaphragms, namely one sealing the sleeve to the shaft, and one sealing the cannula to the sleeve. Then, the lever 134 is engaged by swinging the pusher 136 into place so that its fork end 136a engages the groove 130b in the sleeve 130.

Final closure on the tissue by the purse string clamp jaws is now ready to proceed. The lever 134 is squeezed relative to the handle 132 so that the forked pusher 136 pushes the sleeve 130 with a desired force. The teeth of locking mechanism 132a, 138 engage to hold the lever at the desired position and clamping pressure. The pivotal mounting of the jaws to their support beams via the pins 113a, 115a allows a small amount of clearance about the pins, so that the jaws may be self-levelling as they are squeezed over an irregularly shaped collection of tissue.

The jaws will arrive face to face flat against each other, as the surfaces of the flats 110a, 120a of the support beams 110b, 120 that bear against the undersides of the jaws become parallel as the clamping position is approached. It should be noted that as long as the jaws have been cocked or angled out sufficiently at least approximately 30 degrees to clear the detent action of the beams, the above-noted parallelism will occur even if the jaws are cocked out to any other angle, until beam detent action is reached at the other extreme of cocking. This means that after the jaws are cocked out sufficiently so that their undersides ride on the beam flats, they may function effectively at any angle until rotated to the complementary position, approximately 120 degrees. It should also be noted that the jaws cannot close flat against each other until they have been cocked free of the beam/channel detent system and their undersides ride on the angled flats of the beams.

As the jaws clamp the tubular tissue with the desired degree of force, the opposing rows of teeth 116, 118 bend the tissue between them into a wavelike configuration. Because the tube of tissue is collapsed, a two-wall thickness of the tissue overlies the crest of each tooth.

When the purse string suturing instrument is in place and clamped on the desired section of tissue, the needles 160, each of which are attached to an end of a suture 162, are inserted into the passageways defined by the channels 116a, 118a formed in the teeth 116, 118 of the jaws 112, 114. As each needle travels from tooth to tooth of one jaw, it pierces the wall of tissue that contacts that wall without penetrating the wall of tissue that contacts the other jaw. In this manner, each needle threads the suture through one wall of the two-wall thickness of the tissue and does not sew the tube closed. The needles do not need to be inserted at the same time. After the tip end 160a of each needle, including an end of the suture 162, emerges from the distal end of the jaws, an encircling series of stitches will have been formed in the wall of the tubular tissue.

If the needles 160 are provided with a frangible notch 160c, each tip end 160a can be snapped off with forceps manipulated through a second cannula, for example. The remaining portions of the needles are then withdrawn back through the passageways. The tissue may be cut on one or the other side of the closed jaws.

If the needles are not frangible, the needles are first withdrawn slightly to create a loop in each end of the suture. These loops are snipped and the free ends of the suture are grasped with forceps. Then the entire needles are withdrawn and the suturing instrument is removed in the same manner as above.

To remove the purse string suturing instrument, the lever 134 must be released, the forked pusher 136 must be disengaged from the sleeve slot 130b, and the sleeve 130 must be retracted to its most proximal position. Then the jaws must be cocked back into their detented alignment position with their support beams. Next, the knob 150 is pulled back to retract the beam 120 and jaw 112 assembly by pivoting it back into the recess 110c in the shaft 110. At this time, the assembly is still penetrating through the cannula far enough so that the jaw 112 can be swung all the way back. Now the tool can be withdrawn through the cannula.

FIGS. 27 through 32, 34 and 35 illustrate a third embodiment of the purse string suturing instrument in accordance with the present invention.

Figure 27:
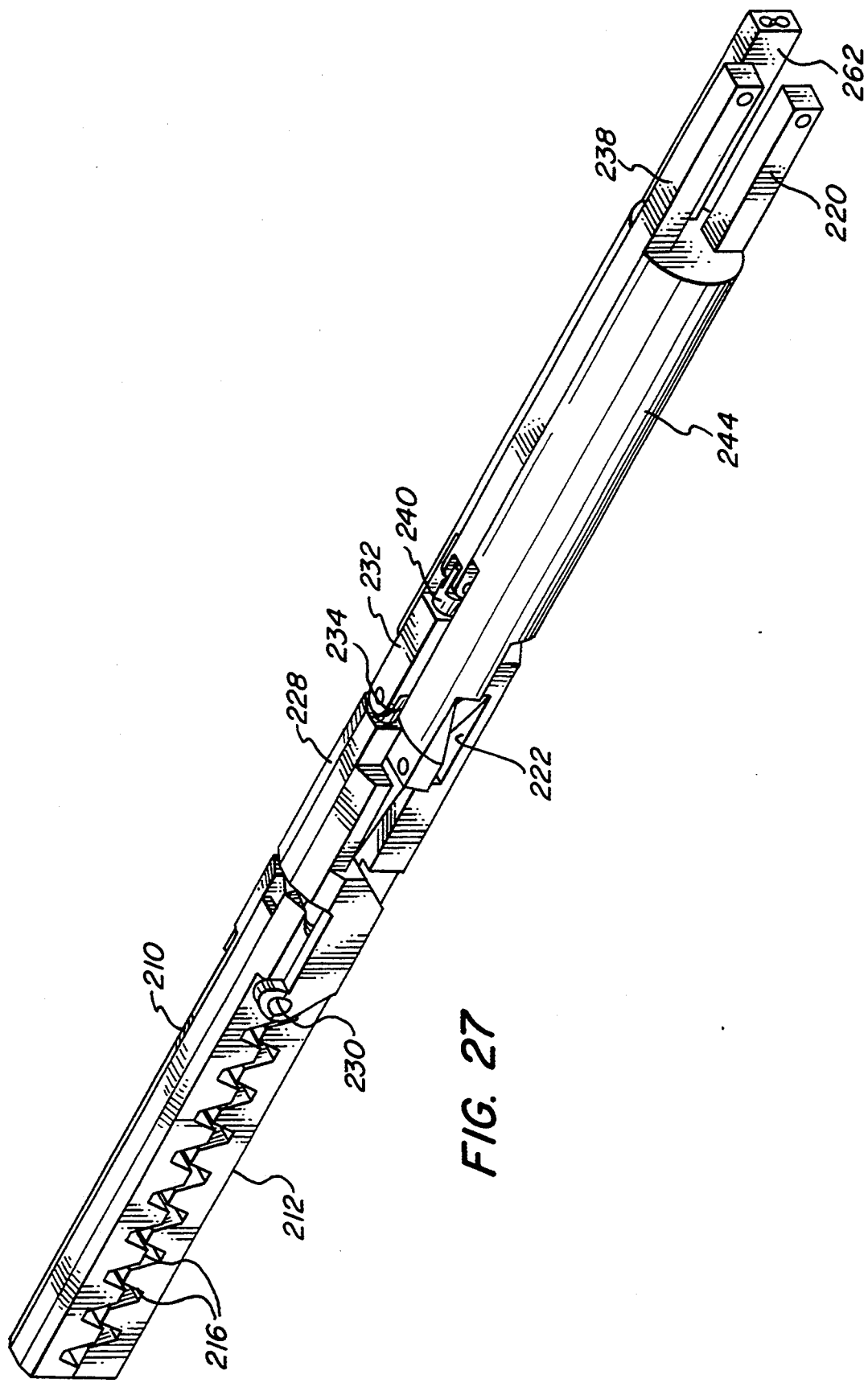
FIG. 27 is an isometric view of the purse string suturing instrument in accordance with a third embodiment of the present invention.
Figure 28:
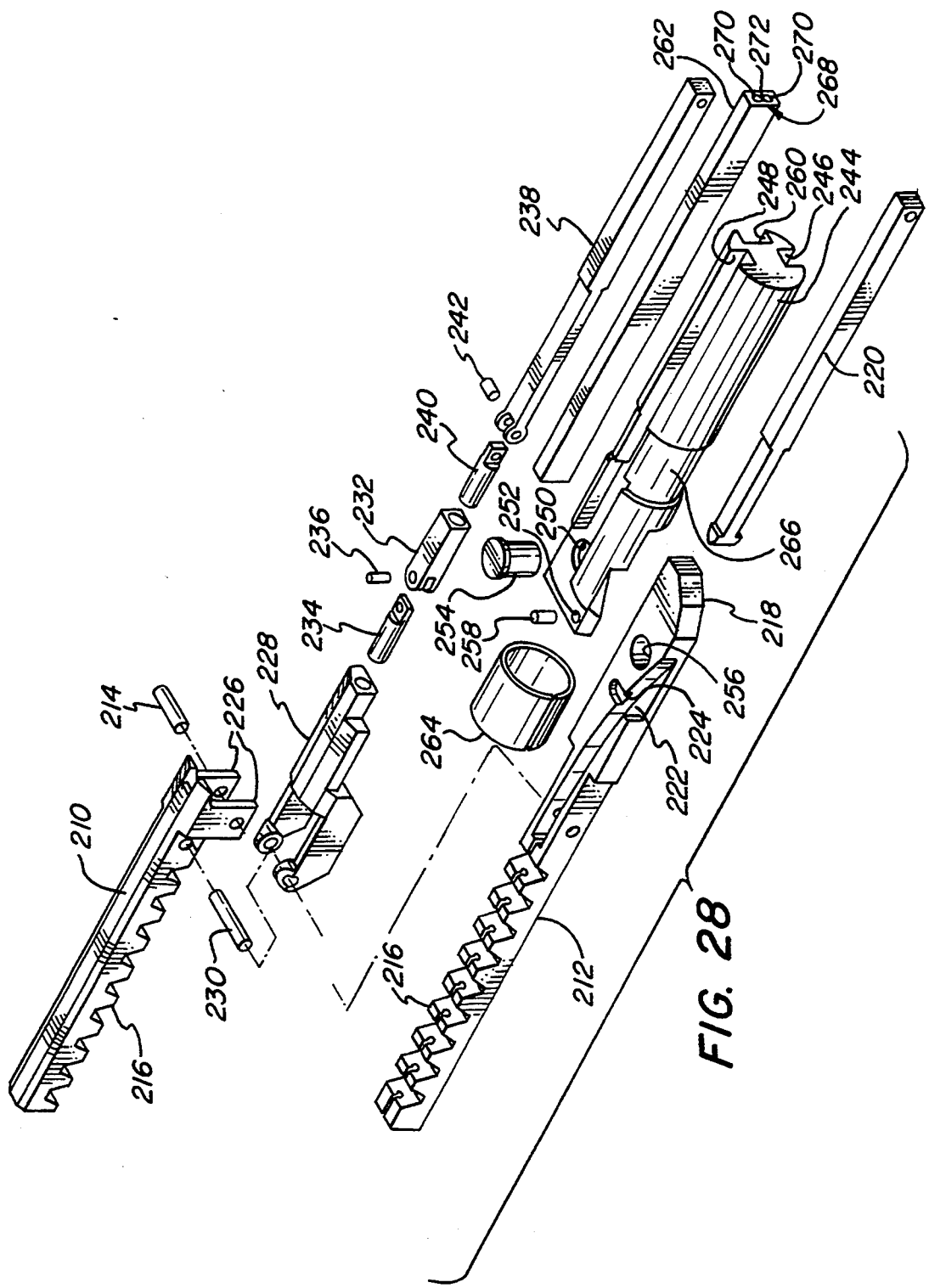
FIG. 28 is an exploded view of the purse string suturing instrument of the third embodiment of the present invention.

With reference initially to FIGS. 27 and 28, the suturing instrument comprises a first jaw 210 and a second jaw 212 connected by pivot pin 214 extending through proximal end extensions 226 of the first jaw for pivoting movement about a first pivot axis. Each jaw includes a row of spaced-apart teeth 216 of uniform size and spacing. The teeth are shaped in the same configuration as the teeth disclosed above in connection with the first and second embodiments and serve to clamp the tissue therebetween in the same manner.

As shown in FIG. 28, the second jaw 212 includes at its proximal end a camming surface 218 to be abutted by a camming rod 220. In addition, the second jaw has a curved pathway 222 for receiving a needle cartridge and a notch 224 for receiving a limit pin in a manner described in detail below.

The first jaw 210 is connected to toggle or lost motion lever 228 by lost motion pin 230 for pivoting movement about a second pivot axis parallel to the first pivot axis. The lost motion lever is connected to a link 232 by a first coupler 234 and link pin 236. The link 232 is also connected to a drive rod 238 by a second coupler 240 and link pin 242. As will be appreciated, each coupler 234 and 240 has one end that is cylindrical. This allows the link 232 to rotate about its longitudinal axis as it pivots about both link pins.

An elongated shaft 244 slidably houses the camming rod 220 and driving rod 238 in elongated slots 246 and 248, respectively. The length of the shaft (and the camming rod and driving rod) is arbitrary, but is generally longer than that shown in FIG. 28. The distal end of the shaft 244 has a large hole 250 and a small hole 252. An articulating pin 254 extends through the large hole 250 and into the same size hole 256 in the second jaw 212 to allow the pair of connected jaws to pivot about a third pivot axis, orthogonal to the first pivot axis, when the camming rod 220 pushes against the camming surface 218. A limit pin 258 extends through the small hole 252 and slides within the notch 224 in the second jaw. The limit pin abuts the closed end of the notch to limit articulation of the jaws in a counter-clockwise direction about the third pivot axis. The underside of the shaft includes a protrusion (unshown) for abutting the camming surface of the second jaw and limiting movement of the jaws in the clockwise direction about the third pivot axis to a position where the jaws are axially aligned with the shaft. The shaft also includes elongated slot 260 for slidably receiving a needle guide, or cartridge, 262, discussed below. A band 264 slips over the shaft to a reduced section 266 thereof to contain the camming rod, the driving rod and the needle guide within their respective slots in the elongated shaft.

The needle cartridge 262 is made of a flexible material, e.g., a suitable polymer plastic, and includes an opening 268 extending axially through its elongated body. The opening is designed to receive two surgical needles and a bioabsorbable surgical thread connected at each end to one of the needles to form a closed loop. The opening therefore has a substantially dog-bone cross-section comprising two circular sections 270 joined by a channel 272. A surgical needle is loaded into each circular section. As will be appreciated, the channel is designed to have a width smaller than the diameter of the needles so the needles cannot slide laterally out of their respective circular sections. As the needles travel axially within the opening as described in detail below, the surgical thread follows the needles by passing through the channel.

The surgical needles preferably used in the three disclosed embodiments of the surgical suturing instrument of the subject invention are shown in detail in FIG. 33. The needle comprises an elongated needle shaft 274 and a pointed needle head 276 connected together by a fragile neck portion 278. The proximal end of the needle shaft 274 has an angled portion 280 to assist the user in pushing the needle through the needle cartridge and the tissue. Other means for pushing the needle, for example, a plastic cap on the end of the needle shaft, are also contemplated. The frangible neck portion is shown in isolation view 33A to have a reduced diameter section formed of two angled sections 278, 280 angled at, for example, 90°, to form a notch. The reduced diameter section is provided to make it easy to snap off the needle head and thread connected thereto from the needle shaft after the thread has been stitched through the tissue.

One way to secure the surgical thread to the needle head is to provide a longitudinal slot 284 in the needle head to receive the thread as shown in isolation view 33C. The needle head is gently crimped to compress the slot around the thread. Another feature of the surgical needle is a longitudinal groove 286 which extends from the slot and continues along the needle shaft as shown in isolation views 33B and 33C. The longitudinal groove (and the slot) are sized to be larger than the surgical thread so the thread can fit within the groove without increasing the overall circumferential size of the needle. In this way, very close tolerances can be maintained between the surgical needle and the needle passageway in the rows of teeth in each jaw. Thus, the groove should be at least as long as the length of the needle passageway.

The sharpened end of the surgical needle can also be provided with cutting edges 288 extending radially outward from the tip 290 of the needle. Isolation view 33D shows three cutting edges 288 equally spaced 120° from each other. The cutting edges cut the tissue as the needle travels therethrough.

FIGS. 34 and 35 illustrate one type of handle assembly for manipulating the camming rod 220 and the driving rod 238. The assembly includes an L-shaped handle 292 secured to the proximal end of the elongated shaft 244. However, for convenience, only the camming rod 220 and driving rod 238 are shown to be connected to the handle assembly. A squeezable L-shaped actuator 294 is pivotally attached to the handle 292 by pivot pin 296 and biased in an upward, or open, position by spring 298. The actuator is connected to the driving rod 238 by a pin 300 and slides the driving rod forwardly when the actuator is squeezed toward the handle. A pivoting stop member 302 is mounted on the underside of the handle and engages an abutting pin 304 on the actuator to stop sliding movement of the driving rod so the jaws are in a closed, but not tightly clamped, position. When the stop member is pivoted out of position so as not to engage the abutting pin (as shown in both FIGS. 34 and 35), the actuator can be fully biased in the upward position to retract the driving rod and open the jaws. A swingable locking member 306 is pivotally attached to the proximal end of the handle and can be swung upwardly to engage a notch 308 in the actuator as shown in FIG. 35. A rotatable knob 310 can be tightened to lock the actuator in its squeezed, or closed, position to tightly clamp the jaws.

A sliding spool 312 is attached to the camming rod 220 by pin 314. The spool slides along rod 316 extending from the handle to actuate the camming rod back and forth. The proximal end of the rod 316 is threaded and includes a locking nut 318 that can be tightened to secure the sliding spool in its forwardmost position.

In use, the suturing instrument is inserted into the body by way of a cannula of, for example, 12 mm, with the jaws closed and axially aligned with the elongated shaft as shown in FIG. 27. To attain this position, the camming rod is retracted toward the handle as far as possible and the driving rod is pulled back almost all the way in a closed jaw position (where the limit pin 304 on the actuator 294 abuts the stop lever 302 on the handle 308) to close the jaws.

Figure 29:
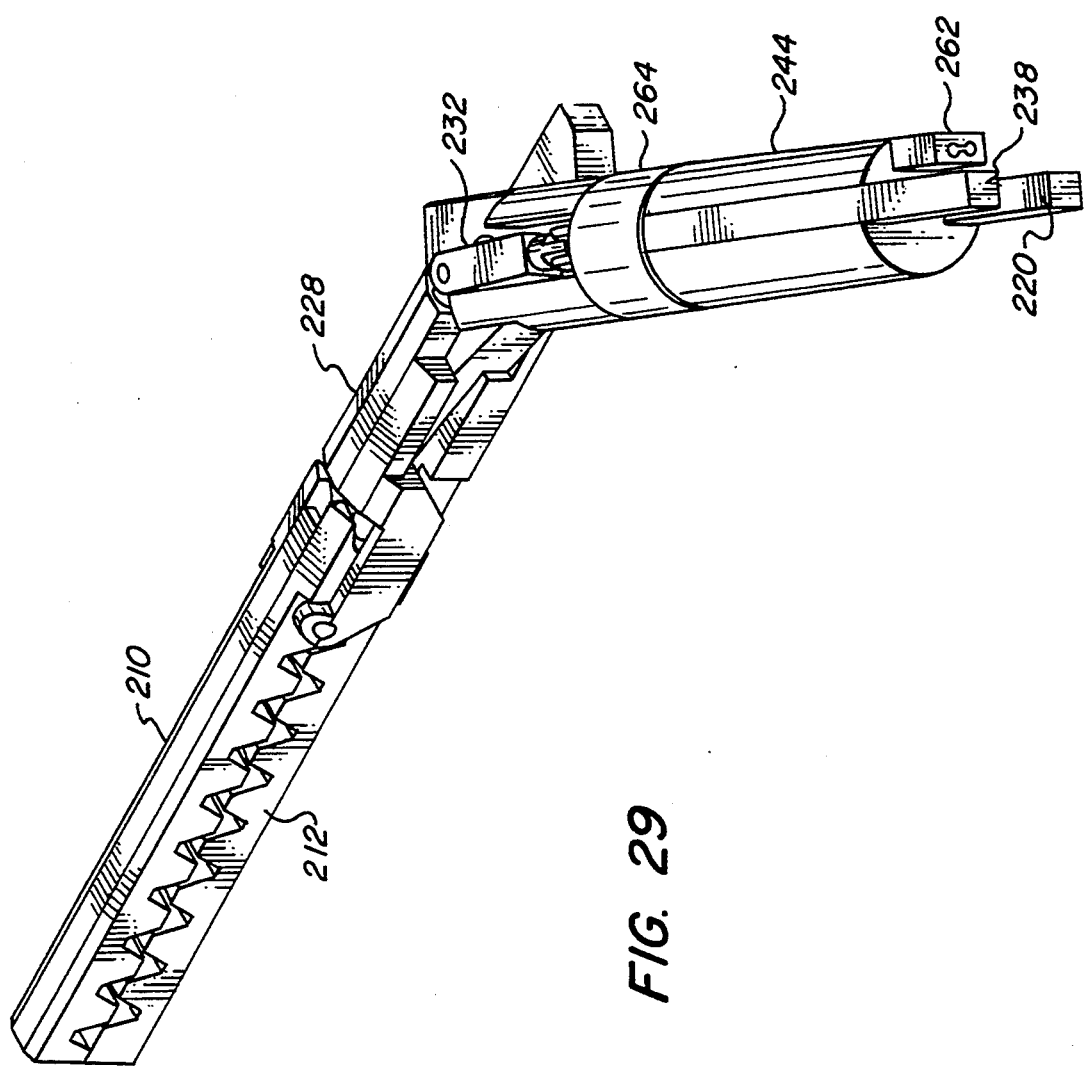
FIG. 29 is an isometric view of the purse string suturing instrument of the third embodiment of the present invention with the jaws closed and in the articulated position.

After the surgical instrument has been inserted through the cannula, the camming rod is slid forwardly by sliding the spool 312 along the rod 316 of the handle. With this action, the distal end of the camming rod abuts the camming surface 218 of the second jaw and articulates, or pivots, the first and second jaws about the actuating pin 254. The jaws are locked in the articulated position as shown in FIG. 29 by turning the locking nut 318 on the rod until it abuts the spool. One advantage of disposing the jaws in the articulated, or angled, position is that it provides the surgeon-user with a better view of the section of the tissue to be clamped. Another advantage of this structure is that it provides accessibility by angling across a body cavity.

Figure 30:
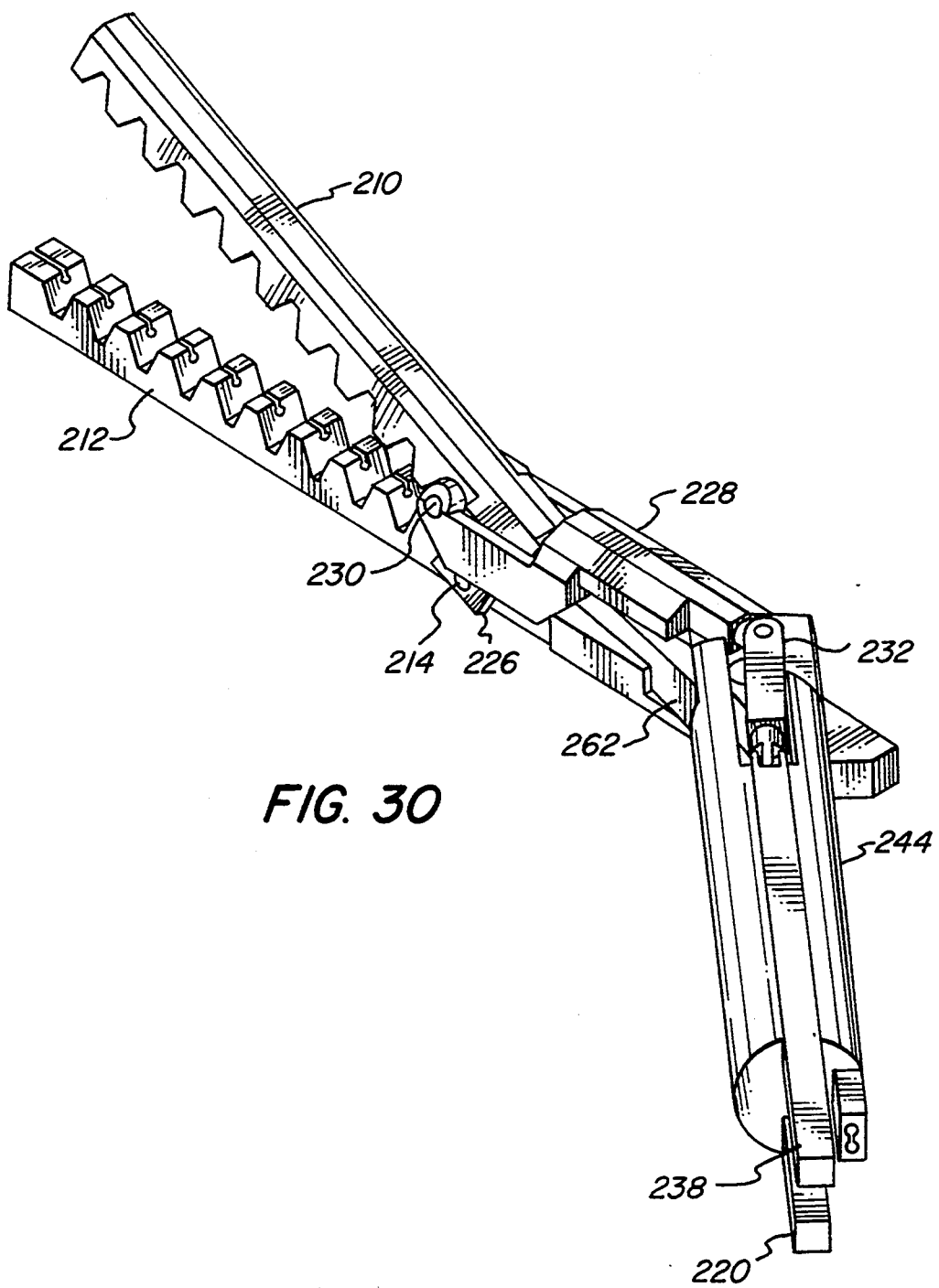
FIG. 30 is an isometric view of the suturing instrument of the third embodiment of the present invention with the jaws open and in the articulated position.

The next step is to open the jaws by fully retracting the driving rod 238. This is accomplished by pivoting the stop lever 302 on the handle so it rotates out of contact with the limit pin 304 on the actuator. The actuator 294 then pivots further about pivot pin 296 by the force of spring 298 to its fully biased position as shown in FIG. 34. Because the lost motion pivot pin 230 is displaced vertically above the jaw pivot pin 214, retraction of the driving rod (and thus the lost motion lever) creates a moment about the jaw pivot pin and allows the jaws to open as shown in FIG. 30.

With the jaws in the open position, the suturing instrument is manipulated to position a tubular anatomic member between and transverse to the open jaws. The jaws are then ready to be closed and clamped around the tubular mender.

Figure 31:
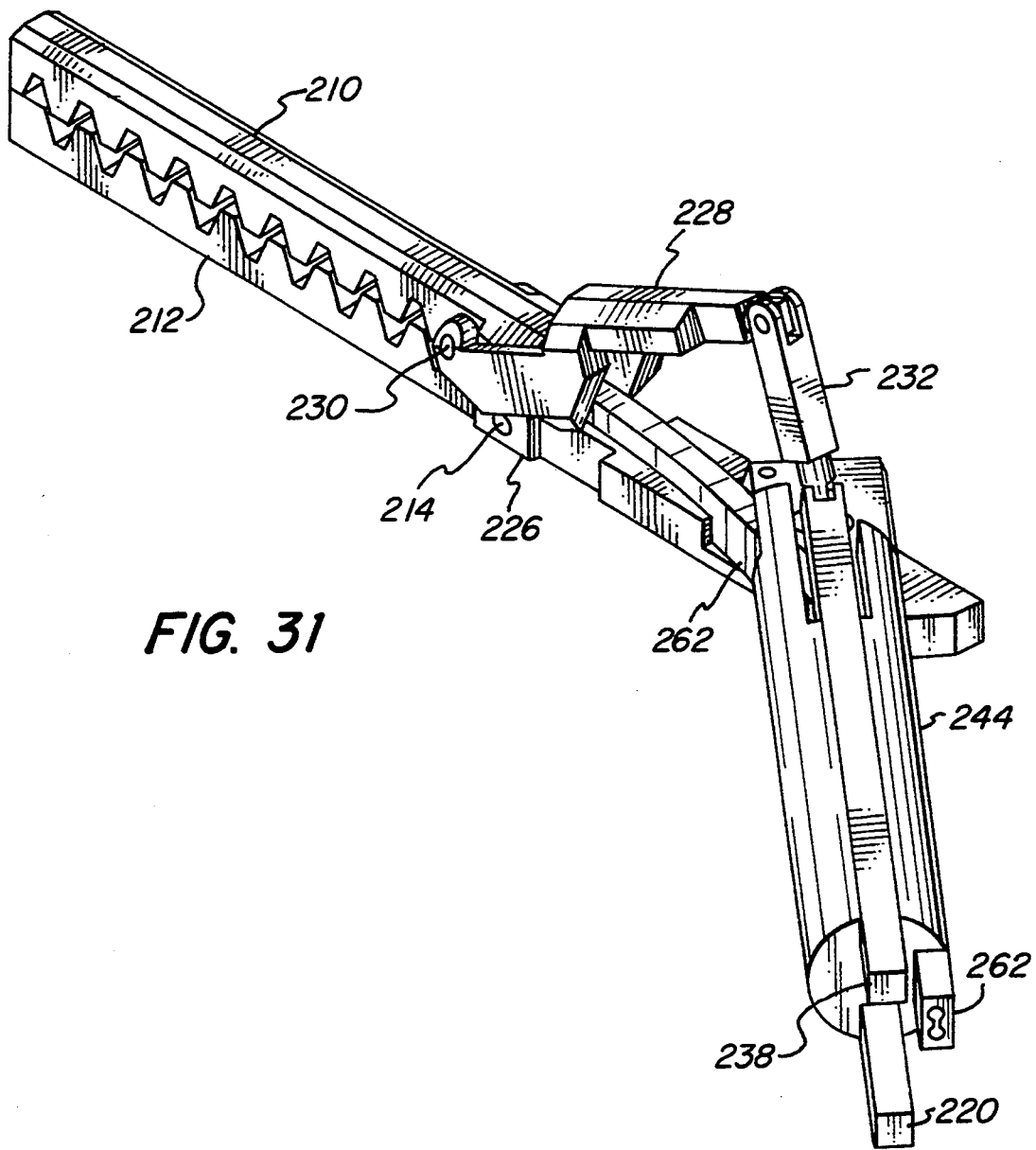
FIG. 31 is an isometric view of the suturing instrument of the third embodiment of the present invention with the jaws in the articulated and clamped positions.
Figure 32:
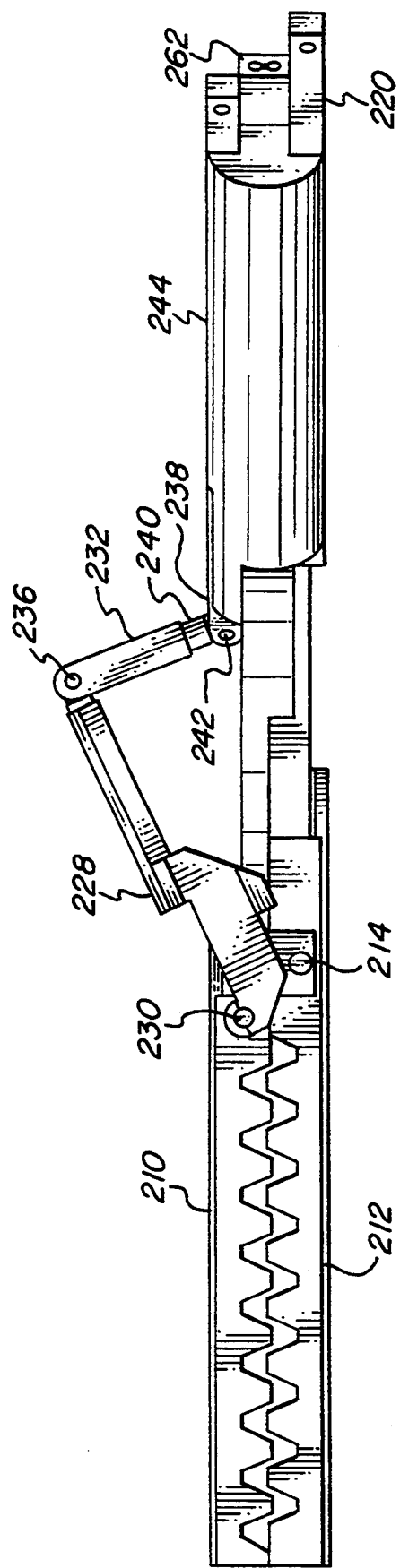
FIG. 32 is a side view of the suturing instrument of the third embodiment of the present invention with the jaws in the articulated and clamped position.

To clamp the jaws the actuator is squeezed to slide the driving rod forwardly, or toward the distal end of the suturing instrument. With reference to FIGS. 31 and 32, this action creates a pivot point about the pivot pin 242 linking the second universal pin 240 (connected to the link 232) and the driving rod 238 and another pivot point about pivot pin 236 linking the first universal pin 234 (connected to the toggle or lost motion lever 228) and the link 232. By virtue of the raised lost motion lever, which creates a longer (and greater) moment arm about the fulcrum, at pin 24, and the orientation between the lost motion pivot pin 230 and the jaw pivot pin 214 (displaced vertically and horizontally), a significant clamping force can be achieved by the jaws to tightly squeeze the tissue therebetween.

Although the needle guide 268 is shown in each of FIGS. 29 through 32 to be protruding into the curved pathway 222 of the second jaw, it is preferable to position the needle cartridge just in the shaft of the suturing instrument until the jaws are clamped around the tissue. The needle cartridge can then be pushed forwardly to extend into the curved pathway and position its distal end against the front row of teeth in the jaws. At this position, the circular portions 270 of the opening 268 in the needle cartridges are aligned with the passageways formed in the teeth.

The surgical needles and suture connected thereto can then be forced forwardly into the passageways to pierce the tissue and form the purse string suture in the same manner discussed above in the first and second embodiments. Preferably, the heads of the needles are snapped-off using forceps and withdrawn, with the suture, through a second cannula in the body. As will be appreciated, the needles and suture can be loaded into the needle cartridge before the cartridge is inserted into the suturing instrument or at any stage after the needle cartridge is placed within its elongated slot in the shaft or in the pathway in the second jaw.

To withdraw the suturing instrument, the actuator is released to the closed jaw position to lower the lost motion lever 228. The clamp nut 318 is released. The jaws are then articulated by, for example, forceps, to axially align them with the elongated shaft. The suturing instrument is then withdrawn from the body through the cannula.

Although specific embodiments of the present invention has been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A method of placing a purse string suture in a section of tubular tissue inside a body cavity of a patient without fully opening the patient, said method comprising the steps of:

inserting a cannula into the body cavity;

inserting, through the cannula, an instrument comprising a pair of relatively movable jaws hinged together at one end for pivotal movement about a first axis, each jaw having a row of spaced apart, uniform-size teeth, each tooth having a base and a crest, the two rows being opposed and offset with respect to each other so that the rows of teeth mesh when the jaws are closed, the crest of each tooth having a channel therein running parallel to the direction of the row, all of the channels in each row being aligned so as to define at their bases a substantially straight needle passageway through all of the teeth in the rows, the instrument being inserted through the cannula with the pair of jaws being closed;

articulating the pair of jaws about a second pivot axis transverse to the first pivot axis;

actuating the first and second jaws to pivot about the first axis to an open position;

positioning the first and second jaws adjacent and transverse to the section of tubular tissue;

actuating the first and second jaws to pivot about the first axis to clamp around the tissue and bend the clamped tissue into a wavelike configuration with a two-wall thickness of the tissue overlying the crest of each tooth, the tissue being forced deep enough into the spaces between the teeth that a first wall thickness of tissue, but not the second wall thickness thereof, protrudes into the needle passageway;

sliding a suturing cartridge having two needles attached to opposite ends of a length of bioabsorbable thread and loaded into a needle cartridge through a pathway in one of the jaws;

forcing the two needles completely through the needle passageways and the tissue, one needle for each passageway, thereby creating an encircling series of stitches in the wall of the tubular tissue; and detaching the needles from the thread and removing the needles from the body, thereby leaving a purse string suture in the tubular tissue, ready to be drawn snug and tied.

2. A surgical suturing instrument for placing a purse string suture in a tubular tissue, said instrument comprising:

a pair of relatively movable jaws for clamping the tubular tissue therebetween, a first jaw of said pair of jaws being pivotable with respect to a second jaw about a first pivot axis, each jaw having a row of spaced-apart, uniform-size teeth;

actuating means for actuating said pair of jaws between an open position for receiving the tubular tissue and a clamping position where the row of teeth of said first jaw meshes with the row of teeth of said second jaw, said actuating means including a toggle linkage having a rigid lever pivotally connected to one of said jaws about a second pivot axis parallel to the first pivot axis, a link pivotally connected to said lever and a driving rod pivotally connected to said link; and articulating means, positioned to contact one of said jaws, for pivoting said pair of jaws about a third pivot axis transverse to the first pivot axis, wherein each tooth includes a base and a crest, the two rows being opposed and offset with respect to each other in the clamping position so that the rows of teeth mesh when the jaws are closed, thereby bending the tubular tissue between the rows of teeth into a wavelike configuration with a two-wall thickness of the tissue overlying the crest of each tooth, and wherein the crest of each tooth includes a channel therein running parallel to the direction of the row, all of the channels in each row being aligned so as to define at their bases a substantially straight passageway for the transit of a thread-pulling needle through all of the teeth in the row, the base of each channel being sufficiently close to the base of the tooth that a needle forced through the passageway when said jaws are clamped across the tissue can run through only the wall of the wave of tissue contacting and overlying the crest of each tooth without penetrating the next adjacent wall of the tissue.

3. A surgical suturing instrument according to claim 2, wherein the cross-section of the channel through each tooth is substantially keyhole-shaped, with a circular section at the base of the channel and a narrower-width slot section extending from the circular section of the crest of said tooth.

4. A surgical suturing instrument according to claim 3, further including first and second needles, one for each row of teeth, each needle having means for attaching thereto an end of a thread to be pulled by said needle, and each said needle having a pointed front end and a blunt rear end for pushing the needle through the passageway, the diameter of each said needle being smaller than the diameter of the circular section of the keyhole-shaped channel with which it is paired but greater than the width of the slot section of the channel.

5. A surgical suturing instrument according to claim 4, further including a length of bioabsorbable thread one end of which is attached to said first needle and the other end of which is attached to said second needle, the diameter of the thread being equal to or less than the width of the slot sections of the channels through the teeth.

6. A surgical suturing instrument according to claim 4, further comprising needle cartridge means for defining a needle guide; said cartridge means including an elongated body formed with two substantially parallel guideways, each having a second cross-sectional shape substantially congruent to the diameter of the circular section of the keyhole-shaped channel, for receiving first and second surgical needles for sliding movement therein; and an open channel joining said guideways throughout their length.

7. A surgical suturing instrument according to claim 6, wherein said needle cartridge means is made of a flexible material and is insertable within a curved pathway in one of said jaws.

8. A surgical suturing instrument according to claim 7, further comprising an elongated shaft having longitudinal notches for slidably housing said camming rod, said driving rod and said needle cartridge, said shaft being connected to said handle means at a first end and said pair of jaws at a second end.

9. A surgical suturing instrument according to claim 2, wherein the width of each tooth, measured in the direction of the row of teeth, is greater at its base than at its crest.

10. A surgical suturing instrument for placing a purse string suture in a tubular tissue, said instrument comprising:

a pair of relatively movable jaws for clamping the tubular tissue therebetween, a first jaw of said pair of jaws being pivotable with respect to a second jaw about a first pivot axis, each jaw having a row of spaced-apart, uniform-size teeth;

actuating means for actuating said pair of jaws between an open position for receiving the tubular tissue and a clamping position where the row of teeth of said first jaw meshes with the row of teeth of said second jaw, said actuating means including a toggle linkage having a rigid lever pivotally connected to one of said jaws about a second pivot axis parallel to the first pivot axis, a link pivotally connected to said lever and a driving rod pivotally connected to said link; and articulating means, positioned to contact one of said jaws, for pivoting said pair of jaws about a third pivot axis transverse to the first pivot axis, wherein said articulating means includes a camming rod slidably disposed to engage one of said jaws and pivot said pair of jaws about the third pivot axis.

11. A surgical suturing instrument according to claim 10, further comprising handle means for sliding said driving rod to actuate said pair of jaws about the first pivot axis and sliding said camming rod to articulate said pair of jaws about the third pivot axis.

12. A surgical suturing instrument according to claim 11, further comprising an elongated shaft for slidably housing said camming rod and said driving rod, said shaft being connected to said handle means at a first end and said pair of jaws at a second end.

13. A surgical suturing instrument according to claim 12, wherein said shaft includes stop means for limiting the articulation of said pair of jaws.

14. A surgical suturing instrument for placing a purse string suture in a tubular tissue, said instrument comprising:
 a pair of relatively movable jaws for clamping the tubular tissue therebetween, a first jaw of said pair of jaws being pivotable with respect to a second jaw about a first pivot axis, each jaw having a row of spaced-apart, uniform-size teeth;
 actuating means for actuating said pair of jaws between an open position for receiving the tubular tissue and a clamping position where the row of teeth of said first jaw meshes with the row of teeth of said second jaw, said actuating means including a toggle linkage having a rigid lever pivotally connected to one of said jaws about a second pivot axis parallel to the first pivot axis, a link pivotally connected to said lever and a driving rod pivotally connected to said link;
 articulating means, positioned to contact one of said jaws, for pivoting said pair of jaws about a third pivot axis transverse to the first pivot axis; and
 a first universal pin connecting said link with said lever and a second universal pin connecting said link with said driving rod, said first and second universal pins allowing said link to rotate about its longitudinal axis and relative to said lever and said driving rod.

15. A medical device, comprising:
 a pair of jaws;
 hinge means for linking said jaws together for relative pivoted movement about a first pivot axis between an open position and a closed position;
 actuating means including a rigid lever, having first and second ends, connected to one said jaw for pivoted movement therewith; an articulated link connected to said second end of said lever; and a driving rod, mounted for reciprocal movement between advanced and withdrawn positions, connected to said link; wherein the interconnection of said driving rod and said one jaw through said lever and said link causes said jaws to move to the closed position when said driving rod is moved to the advanced position and to move to the open position when said driving rod is moved to the withdrawn position; and
 a first universal pin connecting said link with said first end of said lever and a second universal pin connecting said link with said driving rod, said first and second universal pins allowing said link to rotate about its longitudinal axis and relative to said lever and said driving rod.

16. A medical device according to claim 15, wherein said lever is connected to one of said jaws for relative motion therewith about a second pivot axis, said first and second pivot axes being parallel and offset with respect to each other.

* * * * *